United States Patent
Kunishima

(10) Patent No.: US 8,449,979 B2
(45) Date of Patent: May 28, 2013

(54) MOLECULAR AGGREGATE CAPABLE OF UNDERGOING PHASE TRANSITION BY DEHYDRATING CONDENSATION AND METHOD OF PHASE TRANSITION THEREOF

(75) Inventor: Munetaka Kunishima, Hyogo (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 1160 days.

(21) Appl. No.: 11/814,901

(22) PCT Filed: Dec. 12, 2005

(86) PCT No.: PCT/JP2005/023196
§ 371 (c)(1),
(2), (4) Date: Jul. 26, 2007

(87) PCT Pub. No.: WO2006/080157
PCT Pub. Date: Aug. 3, 2006

(65) Prior Publication Data
US 2009/0023003 A1 Jan. 22, 2009

(30) Foreign Application Priority Data
Jan. 28, 2005 (JP) .................. 2005-021241

(51) Int. Cl.
*A61K 38/08* (2006.01)
*C07K 7/00* (2006.01)
(52) U.S. Cl.
USPC ....... 428/402.2; 424/450; 424/94.3; 428/35.7
(58) Field of Classification Search
USPC ............ 424/450, 94.3; 264/4.1, 4.3; 554/103, 554/37; 428/402.2
See application file for complete search history.

(56) References Cited

U.S. PATENT DOCUMENTS
4,911,928 A * 3/1990 Wallach ............... 428/402.2
5,229,104 A * 7/1993 Sottery et al. ............ 424/59
(Continued)

FOREIGN PATENT DOCUMENTS
EP 1138310 A1 3/2000
EP 1085000 A1 3/2001
(Continued)

OTHER PUBLICATIONS
Duzgunes, Nejat et al., "Lipid Mixing during Membrane Aggregation and Fusion: Why Fusion Assays Disagree", Biochemistry, 1987, pp. 8435-8442, vol. 26, American Chemical Society.
(Continued)

*Primary Examiner* — Ellen S Wood
(74) *Attorney, Agent, or Firm* — The Webb Law Firm

(57) ABSTRACT

Provided is a bilayer membrane vesicle capable of undergoing a phase transition. The bilayer membrane vesicle includes: (a) a fatty acid salt having 6 to 20 carbon atoms; (b) an alcohol or an amine compound having an aliphatic chain of 6 to 20 carbon atoms; and (c) an artificial synthetic lipid or a phospholipid capable of forming a bilayer membrane. Preferably, this bilayer membrane vesicle further contains (d) a tertiary amine as a component of the membrane. Also provided is a method of inducing a phase transition of a bilayer membrane vesicle, the method including the step of adding a dehydrating condensing agent or a dehydrating condensing agent precursor having the property of accumulating at an interface to the bilayer membrane vesicle. By causing the lipids that form a molecular aggregate to chemically change, it is possible to change the physical property and the morphology of the molecular aggregate and control the timing of phase transitions such as membrane fusion. In the membrane fusion, for example, fusion can occur without leakage of the contents of the bilayer membrane vesicle.

9 Claims, 6 Drawing Sheets

U.S. PATENT DOCUMENTS

| | | | |
|---|---|---|---|
| 5,468,398 A * | 11/1995 | Farooq et al. | 510/522 |
| 5,756,014 A | 5/1998 | Mathur | |
| 5,874,105 A * | 2/1999 | Watkins et al. | 424/450 |
| 6,387,373 B1 | 5/2002 | Wright et al. | |
| 6,458,948 B1 | 10/2002 | Iwasaki et al. | |
| 2002/0094367 A1 | 7/2002 | Fuglsang et al. | |

FOREIGN PATENT DOCUMENTS

| | | | |
|---|---|---|---|
| EP | 1138310 A1 | 10/2001 | |
| FR | 2803202 A1 | 1/2000 | |
| FR | 2803202 A1 | 7/2001 | |
| FR | 2842734 A1 | 7/2002 | |
| FR | 2842734 A1 | 1/2004 | |
| GB | 2379386 A | 3/2003 | |
| JP | 7242680 A | 9/1995 | |
| JP | 9511521 A | 11/1997 | |
| JP | 2001089360 | 3/2001 | |
| JP | 2001089360 | 4/2001 | |
| JP | 2005298407 A | 10/2005 | |
| WO | 9416061 | 7/1994 | |
| WO | 9522989 | 8/1995 | |
| WO | 9527478 A1 | 10/1995 | |
| WO | 0053544 A1 | 9/2000 | |
| WO | 0219828 A1 | 3/2002 | |
| WO | WO03047499 | * | 7/2003 |

OTHER PUBLICATIONS

Lentz, Barry R. et al., "Bilayer Curvature and Certain Amphipaths Promote Poly(ethylene glycol)-Induced Fusion of Dipalmitoylphosphatidylcholine Unilamellar Vesicles", Biochemistry, 1992, pp. 2643-2653, vol. 31, American Chemical Society.

Yang, Qiao Li et al., "Effects of Lipid Headgroup and Packing Stress on Poly(Ethylene Glycol)-Induced Phospholipid Vesicle Aggregation and Fusion", Biophysical Journal, Jul. 1997, pp. 277-282, vol. 73, Biophysical Society.

Blumenthal, Robert et al., "Fluorescent lipid probes in the study of viral membrane fusion", Chemistry and Physics of Lipids, 2002, pp. 39-55, vol. 116, Elsevier Science Ireland Ltd.

Sugar, Istvan P. et al., "Model of cell electrofusion, Membrane electroporation, pore coalescence and percolation", Biophysical Chemistry, 1987, pp. 321-335, vol. 26, Elsevier Science Publishers B.V. (Biomedical Division).

Kulin, Simone et al., "Optical Manipulation and Fusion of Liposomes as Microreactors", Langmuir, 2003, pp. 8206-8210, vol. 19, American Chemical Society.

Kim, Jeongha et al., "Fusion of Phospholipid Vesicles Induced by alpha-Lactalbumin at Acidic pH", Biochemistry, 1986, pp. 7867-7874, vol. 25, American Chemical Society.

Takakura, Katsuto et al., "Morphological Change of Giant Vesicles Triggered by Dehydrocondensation Reaction", Chemistry Letters 2002, 2002, pp. 404-405, The Chemical Society of Japan.

Toyota, Taro et al., "Temporal Emergence of Giant Vesicles Accompanied by Hydrolysis of Ammonium Amphiphiles with a Schiff-base Segment", Chemistry Letters, 2004, pp. 1442-1443, vol. 33, The Chemical Society of Japan.

Nieve, Jose-Luis et al., "Liposome Fusion Catalytically Induced by Phospholipase C", Biochemistry, 1989, pp. 7364-7367, vol. 28, American Chemical Society.

Ohki, Kazuo, "Relationship between Physical Properties of Lipids Preferring Non-bilayer Membranes and Functions of Biomembranes", Seibutsu Butsuri, 2004, pp. 161-165, vol. 44(4).

Schmidt, Anne et al., "Endophilin I mediates synaptic vesicle formation by transfer of arachidonate to lysophosphatidic acid", Nature, Sep. 9, 1999, pp. 133-141, vol. 401, Nature.

Kunishima, Munetaka et al., "Formation of carboxamides by direct condensation of carboxylic acids and amines in alcohols using a new alcohol- and water-soluble condensing agent: DMT-MM", Tetrahedron, 2001, pp. 1551-1558, vol. 57, Elsevier Science Ltd.

* cited by examiner

◆: Addition of methanol only   □: Addition of CDMT 50 equivalents
▲: Addition of CDMT 50 equivalents + no tertiary amine ◆: Addition of methanol only   □: Addition of CDMT 25 equivalents
▲: Addition of CDMT 50 equivalents ◆: Addition of methanol only   □: Addition of CDMT 25 equivalents
▲: Addition of CDMT 50 equivalents

MOLECULAR AGGREGATE CAPABLE OF UNDERGOING PHASE TRANSITION BY DEHYDRATING CONDENSATION AND METHOD OF PHASE TRANSITION THEREOF

TECHNICAL FIELD

The present invention relates to molecular aggregates capable of undergoing a phase transition through dehydrating condensation at a water interface, and phase transition methods of the same. More specifically, it relates to methods of inducing fusion or fission of molecular aggregates such as liposomes at a water interface.

BACKGROUND ART

To cause a change in a state of molecular aggregation, generally the concentration of the surfactant or temperature is changed. In an equilibrium system such as a micelle, the state can be rapidly changed by adding a different type of surfactant.

On the other hand, in dispersed systems such as bilayer membrane vesicles, of which liposomes are a representative example, lipids that constitute the dispersed system are in a relatively stable state and thus transfer very slowly. To induce fusion or fission of these aggregates, generally a change in a physical state of an interface is occurred. Such a change is highly dependant on the lipids to be used, the reaction conditions and the like and often there are limitations.

For example, liposomes composed of phosphatidylserine can be made to undergo a phase transition such as membrane fusion by adding $Ca^{2+}$ (Duzgunes et al., Biochemistry, (1987) vol. 26, pp. 8435-8442). It is believed that this is because $Ca^{2+}$ causes charge neutralization, crosslink between lipids, and dehydration so that the membrane becomes unstable. However, this method cannot be employed for liposomes composed of only neutral phospholipids. It has also been reported that membrane fusion occurs upon adding high concentration of polyethylene glycol to liposomes composed of phosphatidylcholine (Lentz et al. Biochemistry, (1992) vol. 31, pp. 2643-2653, and Yang et al., Biophysical Journal, (1997) vol. 73, pp. 277-282). This fusion is caused by destabilization of the membrane due to loss of the free water in the membrane. A membrane fusion method by utilizing viruses also has been proposed (Blumenthal et al., Chemistry and Physics of Lipids, (2002) vol. 116, pp. 39-55). This method requires receptors against virus outside the membrane. Other reported methods include a method of inducing membrane fusion via physical stimulus caused by an electrical pulse (Sugar et al., Biophysical Chemistry, (1987) vol. 26, p. 321) and a method of membrane fusion by irradiating UV light on adhered liposomes (Kulin et al., Langmuir, (2003) vol. 19, pp. 8206-8210). There is also a method of adding protein or peptide to cause a change in the higher-order structure due to pH-dependant protonization and thereby inducing membrane fusion (Kim et al., Biochemistry, (1986) vol. 25, pp. 7867-7874).

Every one of these various fusion methods is based on a change in the physical state of the lipids forming the molecular aggregate, and requires aggregation at a previous stage of fusion. In other words, when lipids alone are dispersed, the lipids themselves that constitute the molecular aggregate are in a completely inactivated state.

On the other hand, there has been reported phase transitions of the membrane, such as fusion and fission, based on chemical reaction (Takakura et al., Chemistry Letters, (2002) pp. 404-405, and Toyota et al., Chemistry Letters, (2004) vol. 33, pp. 1442-1443). Specifically, imine formation and subsequent hydrolysis thereof due to dehydrating condensation in the bilayer membrane of the vesicle cause to morphological change in the vesicle and thus leads to membrane fusion and fission. For example, when a dispersion of micelle of amphipathic lipids having a hydrophilic reactive group (amino group) is added to a dispersion of vesicles composed of amphipathic lipids having a hydrophobic reactive group (aldehyde group), an imine is produced through reversible dehydrating condensation between the reactive groups in the membrane bilayer, so that the vesicles become larger (Takakura et al., ibid.). Further, depending on the abundance ratio of the lipids having these reactive groups and the amphipathic lipids produced by dehydrating condensation, a reversible morphological change in the vesicles has been observed (Toyota et al., ibid.). However, these methods do not allow the state of the bilayer membrane of the vesicles to be controlled.

There also are methods of causing fusion by changing the lipid structure through biological means using enzymes. Specifically, these methods involve hydrolyzing phosphatidylcholine or phosphatidylethanolamine with phopholipase C (Nieva, J. L., et al., Biochemistry, (1989) vol. 28, pp. 7364-7367) or hydrolyzing sphingomyelin with sphingomyelinase (Kazuo Ooki, Seibutsu Butsuri, (2004) vol. 44, pp. 161-165) to remove the phosphate group of the phospholipid constituting the bilayer membrane of the vesicle, thereby producing diacylglycerol or ceramide, respectively. In either case, the morphology of the molecule changes from an inverse cone shape to a cylinder in which the molecular area of the polar head portion is small (the critical load parameter changes), so that the curvature alters to cause fusion.

Biological research has shown that the activity of enzymes that acylate single-strand phospholipids to convert them to double-strand phospholipids is increased when membrane fusion or fission is caused (Schmidt, A., et al., Nature, (1999) vol. 401, pp. 133-141). That is to say, it has been shown that in nerve terminal synapses, lysophosphatidic acid (LPA) acyltransferase is essential for reconstituting synapse vesicles. This enzyme transfers an acyl group to LPA, which is monoacylglycerol bonded with a phosphate (single-strand phospholipid), to convert it to a double-stranded phospholipids. Since this reaction occurs when the membrane undergoes a change, it is suggested that the change in curvature in the membrane caused by such enzymatic chemical reactions is important.

SUMMARY OF THE INVENTION

It is an object of the present invention to provide a method for allowing to changing the physical property and the morphology of the molecular aggregate and controlling the timing of phase transitions such as membrane fusion, by chemically changing the lipids that constitute a molecular aggregate.

The method of inducing a phase transition of a bilayer membrane vesicle according to the present invention is based on the fact that by chemically performing dehydrating condensation in molecular aggregates (liposomes) that include a surfactant having an amine or carboxylate polar head portion, the critical load parameter of the lipids is changed and as a result the curvature of the bilayer membrane of the liposome alters, thereby causing strain in the liposome.

The present invention provides a bilayer membrane vesicle, comprising, as components of the membrane:
(a) a fatty acid salt having 6 to 20 carbon atoms;
(b) an alcohol or an amine compound having an aliphatic chain of 6 to 20 carbon atoms; and (c) an artificial synthetic lipid or a phospholipid capable of forming a bilayer membrane.

In an embodiment, the (b) alcohol or amine compound is a dihydric alcohol represented by the following formula I:

$$R^1-NH-CH_2-CH(OH)-CH_2OH \quad (I)$$

wherein $R^1$ is an alkyl group having 6 to 20 carbon atoms, an alkenyl group having 6 to 20 carbon atoms, or an alkynyl group having 6 to 20 carbon atoms.

In a more preferred embodiment, the bilayer membrane vesicle further comprises as a component of the membrane:

(d) a tertiary amine represented by the following formula II:

(II)

wherein one or two of $R^2$, $R^3$, and $R^4$ is a methyl group, and the remaining $R^2$, $R^3$, and $R^4$ is each independently $-CH_2COOC_nH_{2n+1}$, $-C_nH_{2n+1}$, or $-C_6H_4$-p-$C_nH_{2n+1}$, where n is an integer of 6 to 20, and $-C_nH_{2n+1}$ is linear.

In an embodiment, the mole ratio of the (a) fatty acid salt and the (b) alcohol or amine compound is 1:1.

In a further embodiment, the mole ratio of the (a) fatty acid salt, the (b) alcohol or amine compound, and the (c) artificial synthetic lipid or phospholipid capable of forming a bilayer membrane is 1:1:1.

In an embodiment, the (c) artificial synthetic lipid or phospholipid capable of forming a bilayer membrane is a phospholipid.

The present invention also provides a method of inducing a phase transition of a bilayer membrane vesicle, comprising:
preparing a bilayer membrane vesicle, in which the bilayer membrane vesicle comprises as components of the membrane:
(a) a fatty acid salt having 6 to 20 carbon atoms;
(b) an alcohol or an amine compound having an aliphatic chain of 6 to 20 carbon atoms; and
(c) an artificial synthetic lipid or a phospholipid capable of forming a bilayer membrane; and
adding a dehydrating condensing agent or a dehydrating condensing agent precursor to the bilayer membrane vesicle.

In one embodiment, the (b) alcohol or amine compound is a dihydric alcohol represented by the following formula I:

$$R^1-NH-CH_2-CH(OH)-CH_2OH \quad (I)$$

wherein $R^1$ is an alkyl group having 6 to 20 carbon atoms, an alkenyl group having 6 to 20 carbon atoms, or an alkynyl group having 6 to 20 carbon atoms.

In a further embodiment, the bilayer membrane vesicle further comprises as a component of the membrane:

(d) a tertiary amine represented by the following formula II:

(II)

wherein one or two of $R^2$, $R^3$, and $R^4$ is a methyl group, and the remaining $R^2$, $R^3$, and $R^4$ is each independently $-CH_2COOC_nH_{2n+1}$, $-C_nH_{2n+1}$, or $-C_6H_4$-p-$C_nH_{2n+1}$, where n is an integer of 6 to 20, and $-C_nH_{2n+1}$ is linear; and wherein the dehydrating condensing agent precursor is a cyanuric acid derivative represented by the following formula III:

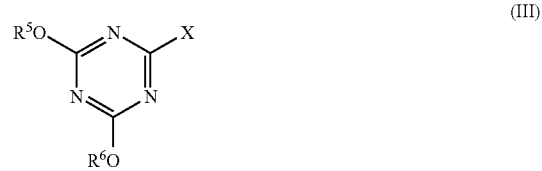

(III)

wherein $R^5$ and $R^6$ are each independently a methyl group, an ethyl group, a hydroxyalkyl group having 2 to 5 carbon atoms, $-(CH_2CH_2O)_mR^7$ (where m is an integer from 1 to 120, and $R^7$ is a hydrogen atom, a methyl group, an ethyl group, or a propyl group), $-(CH_2CH_2NR^8)_mH$ (where m is an integer of 1 to 120, and $R^8$ is an alkyl group having 2 to 5 carbon atoms, an N,N-dialkylaminoethyl group, or $-CH_2CH_2N^+(CH_3)_3$), $-CH_2CH_2SO_3^-$, $-CH_2CH_2N^+(CH_3)_3$, or an alkyl group having 6 to 20 carbon atoms, but both $R^5$ and $R^6$ are not an alkyl group having 6 to 20 carbon atoms at the same time; and X is a halogen atom.

In an embodiment, at least one of $R^5$ and $R^6$ in the formula III is a methyl group or an ethyl group.

In one embodiment, n in the formula II is 12 to 16.

According to the method of the present invention, the dehydrating condensation reaction is utilized to chemically change the lipids that constitute a molecular aggregate composed of a bilayer membrane vesicle so as to change the physical property and the morphology of the molecular aggregate, and thereby it is possible to control the timing of phase transitions such as membrane fusion. In other words, in a bilayer membrane vesicle, it becomes possible to induce a phase transition (fusion or fission) of the molecular aggregate. Consequently, it is possible to provide a vesicle in an activated or a semi-stable state. The bilayer membrane vesicle of the present invention can be preferably used to induce such phase transitions.

DETAILED DESCRIPTION OF THE INVENTION

In the present invention, a suitable amphiphile that has been introduced into the bilayer membrane of a vesicle can be dehydrated and condensed by a dehydrating condensing agent in order to change the state of the bilayer membrane.

Figure 1:
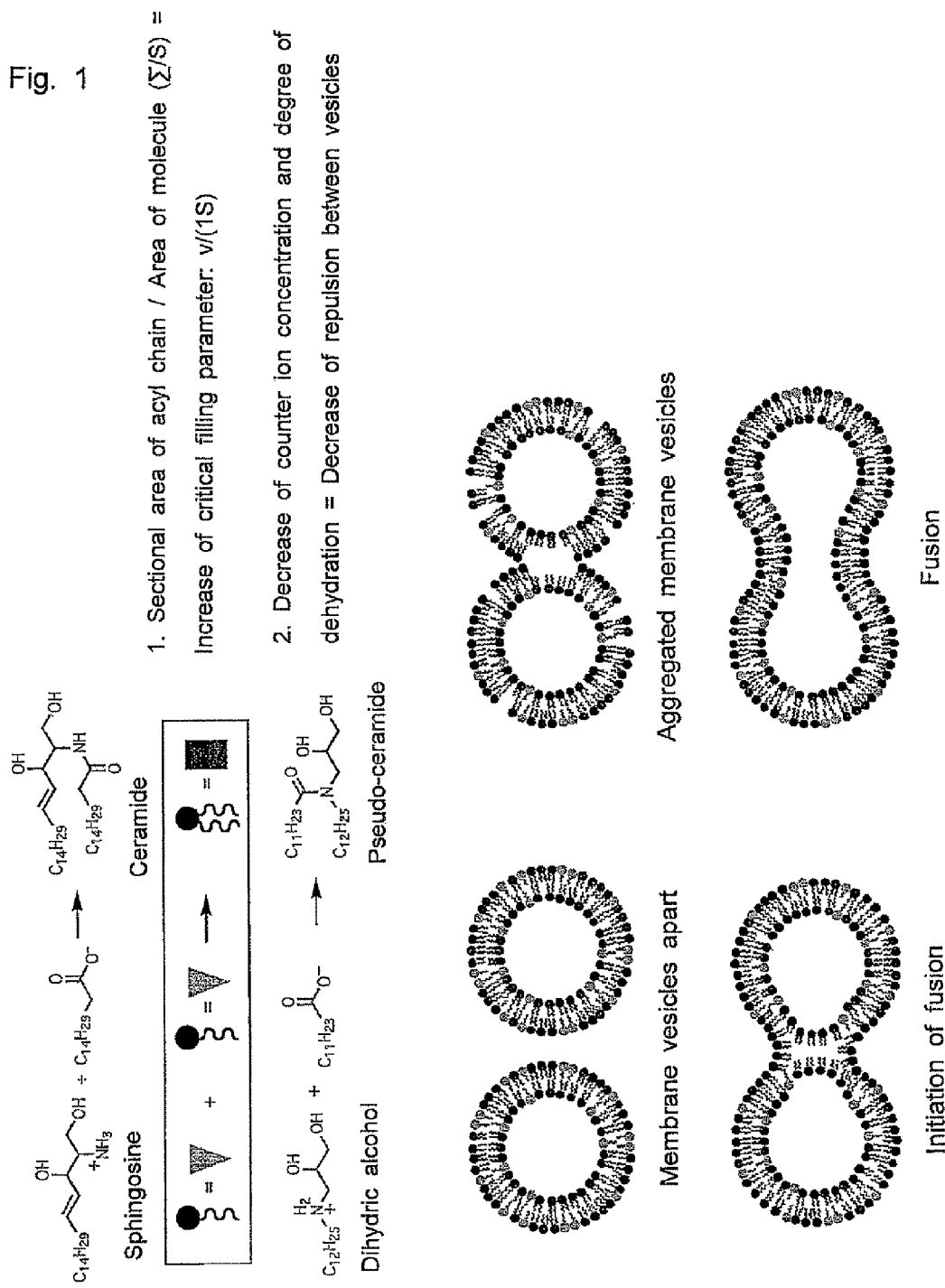
FIG. 1 is a schematic view for explaining the principle of the present invention.

The principle of the present invention is described based on FIG. 1. General surfactants are inverse cone-shaped surfactants in which, as shown by the inverse triangles in the drawing, the large polar head portion is a charged amine or carboxylate. In ceramide in which these surfactants have been subject to dehydrating condensation, because there is a difference in the number of acyl chains (or alkyl chains) of the amphiphile and the charge of the polar head portion or the type of the functional group before and after the reaction, and for example, in the reaction the loss of charge results in a smaller polar head portion, and the ceramide becomes a cylindrical or conical lipid as shown by the rectangle in the drawing. Accordingly, when dehydrating condensation is caused in molecular aggregates containing an amine and a carboxylate (such as liposomes), a change occurs in the curvature of the membrane, for instance, due to the increase in the critical load parameter and the reduced repulsion between membranes, and it is thought that the membranes ultimately fuse together to ease such a change. A specific example is ceramide synthesis from sphingosine. However, because it is difficult to obtain large quantities of sphingosine, the above principle is preferably confirmed by using a dihydric alcohol such as that shown in the drawing as an analogous compound and by condensing the dihydric alcohols to synthesize a pseudo-ceramide, for example.

The method of the present invention may be widely applicable for substrates capable of forming ceramide analogs by dehydrating condensation. Examples of such substrates include various amphipathic fatty acid salts and primary and secondary amines. In particular, to maintain the amphipathicity of the pseudo-ceramide produced, it is preferable that, in addition to the carboxyl group, amine group, or hydroxyl group that undergoes dehydrating condensation, a hydrophilic functional group is present near the polar head portion of any of the carboxylic acid, the amine, or the alcohol compound. This hydrophilic functional group preferably is a neutral group such as a hydroxyl group or a sugar, but it may also be an ion such as a quaternary ammonium ion, a phosphate ion, a sulfonate ion, or a sulfate ion, which are the polar head portions of general surfactants.

The present invention is described in more detail below.

As described above, the present invention provides a bilayer membrane vesicle capable of undergoing a phase transition, and the phase transition method thereof. In the present invention, "phase transition" is not limited to the phase transition of the membrane of a bilayer membrane vesicle. For example, it also includes various morphological changes in the molecular aggregate phase, such as membrane fusion and membrane fission of a bilayer membrane vesicle, a change from a bilayer membrane vesicle to a planar bilayer membrane or a micelle, or a change from a micelle to a bilayer membrane vesicle.

A bilayer membrane vesicle of the present invention contains the followings as components of the membrane:
(a) a fatty acid salt having 6 to 20 carbon atoms;
(b) an alcohol or an amine compound having an aliphatic chain with 6 to 20 carbon atoms; and
(c) an artificial synthetic lipid or a phospholipid capable of forming a bilayer membrane.

There are no particular limitations regarding the fatty acid salts having 6 to 20 carbon atoms (a), as long as the are amphipathic fatty acid salts having property of accumulating at a water interface. Such a fatty acid salt preferably includes those having a lipophilic group such as a long-chain alkyl group, and more preferably linear, branched, or cyclic fatty acid having about 10 to about 20 carbon atoms. Specific examples include salts of caprinic acid (decanoic acid), undecanoic acid, lauric acid (dodecylic acid), myristic acid, palmitic acid, palmitoleic acid, stearic acid, oleic acid, elaidic acid, petroselinic acid, linoleic acid, α-linolenic acid, γ-linolenic acid, icosanic acid, icosatrienoic acid, and arachidonic acid. Examples of salts of these usually include sodium salts and potassium salts. As necessary, these compounds may have the above-described hydrophilic functional group near or proximate to their carboxyl group.

There are no particular limitations regarding the alcohol or amine compounds with an aliphatic chain having 6 to 20 carbon atoms (b), as long as they are amphipathic compounds having a group (such as a hydroxyl group or an amino group) capable of dehydrating condensation with the carboxyl group of the fatty acid salt (a), and also having property of accumulating at a water interface. Preferably, they have a lipophilic group such as a long-chain alkyl group, and more preferably the above-described hydrophilic functional group near or proximate to the group capable of dehydrating condensation. It should be noted that if the fatty acid salt (a) does not have a hydrophilic functional group other than the carboxyl group that undergoes dehydrating condensation, then the compound (b) more preferably has additional hydrophilic functional groups near its polar head portion.

A preferable example of such a compound is a dihydric alcohol represented by the following formula I:

$$R^1\text{—NH—CH}_2\text{—CH(OH)—CH}_2\text{OH} \quad (I)$$

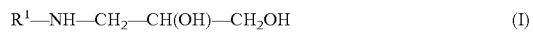

(wherein $R^1$ is an alkyl group having 6 to 20 carbon atoms, an alkenyl group having 6 to 20 carbon atoms, or an alkynyl group having 6 to 20 carbon atoms). In the dihydric alcohol, the amine portion corresponds to the group capable of dehydrating condensation, and the alcohol portion corresponds to the hydrophilic functional group.

In a case where $R^1$ in the dihydric alcohol (b) represented by Formula I is an alkyl group having 6 to 20 carbon atoms, the alkyl group can be linear, branched, or cyclic. Preferably it is linear and has about 10 to about 20 carbon atoms. Examples of such an alkyl group include n-decyl, n-dodecyl (lauryl), n-hexadecyl, and n-octadecyl. In a case where $R^1$ is an alkenyl group having 6 to 20 carbon atoms, the alkenyl group can be linear, branched, or cyclic. Preferably it is linear and has about 10 to about 20 carbon atoms. Examples of such an alkenyl group include 1-decenyl, 1-dodecenyl, 9-hexadecenyl, and 9-octadecenyl. In a case where $R^1$ is an alkynyl group having 6 to 20 carbon atoms, the alkynyl group can be linear, branched, or cyclic. Preferably it is linear and has about 10 to about 20 carbon atoms. Examples of such an alkynyl group include 1-decynyl, 1-dodecynyl, 9-hexadecynyl, and 9-octadecynyl.

There are no limitations regarding the artificial synthetic lipid or phospholipid capable of forming the bilayer membrane (c), as long as they are compounds capable of forming a bilayer membrane.

Examples of the artificial synthetic lipid include long-chain dialkyl compounds, monoalkyl surfactants, and triple-stranded surfactants. For example, examples are shown in "Liposome", edited by Shoshichi Nojima, et al., Nankodo, 1988, pp. 302-309. In general, a compound having two long-chain C12 to C15 alkyl groups and a hydrophilic functional group (cationic, anionic, or nonionic, for example) in the same molecule is preferable, and typically, example thereof is a C12 to C15 dialkyl ammonium salt.

There are no particular limitations regarding the phospholipid, and it may be either a glycerophospholipid or a sphingophospholipid. Examples of such a phospholipid include phosphatidylcholine (lecithin), phosphatidylethanolamine, phosphatidylserine, phosphatidylinositol, phosphatidylglycerol, and sphingomyelin. Preferably, it is phosphatidylcholine.

The bilayer membrane vesicle of the present invention may further include optionally (d) a tertiary amine represented by the following formula II as a component of the membrane:

(II)

(wherein one or two of $R^2$, $R^3$, and $R^4$ is a methyl group, and the remaining $R^2$, $R^3$, and $R^4$ is each independently $-CH_2COOC_nH_{2n+1}$, $-C_nH_{2n+1}$, or $-C_6H_4$-p-$C_nH_{2n+1}$, where n is an integer from 6 to 20, and $-C_nH_{2n+1}$ is linear). In $-CH_2COOC_nH_{2n+1}$, $-C_nH_{2n+1}$, or $-C_6H_4$-p-$C_nH_{2n+1}$, which is the $R^2$, $R^3$, and $R^4$ of the tertiary amine (d) represented by the formula II, n is an integer from 6 to 20, and $-C_nH_{2n+1}$ is linear. Examples of these substituents include n-octyloxycarbonylmethylene, n-decyloxycarbonylmethylene, n-dodecyloxycarbonylmethylene, and n-hexadecyloxycarbonylmethylene; n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, and n-eicocyl; p-(n-hexyl)phenylene, p-(n-octyl)phenylene, p-(n-decyl)phenylene, p-(n-dodecyl)phenylene, p-(n-tetradecyl)phenylene, p-(n-hexadecyl)phenylene, and p-(n-octadecyl)phenylene. In view of ease for introducing into the bilayer membrane vesicle of the present invention, the n in $R^2$, $R^3$, and $R^4$ of the formula II is preferably from 8 to 18, and more preferably from 12 to 16.

Regarding $R^2$, $R^3$, and $R^4$ of the formula II, in view of the reactivity of the dehydrating condensation of the method according to the present invention, one or two of $R^2$, $R^3$, and $R^4$ is (are) a methyl group, and the remaining $R^2$, $R^3$, and $R^4$ is (are) a group having a linear alkyl group with 6 to 20 carbon atoms. More preferably two of $R^2$, $R^3$, and $R^4$ are methyl groups. It is not preferable that all of $R^2$, $R^3$, and $R^4$ are groups having linear alkyl groups with 6 to 20 carbon atoms because the reaction efficiency is not good.

In a case where the tertiary amine represented by the formula II is contained as a component of the membrane of the bilayer membrane vesicle, it is preferable to use a cyanuric acid derivative represented by the formula III, which is a dehydrating condensation agent precursor and is described in detail later.

There are no particular limitations regarding the relative amount of compounds (a) through (d) in the bilayer membrane vesicle of the present invention, as long as the vesicle can be formed. The substrates for the dehydrating condensation reaction, that is, the fatty acid salt (a) and the alcohol or amine compound (b) are preferably used in a mole ratio of about 1:1. More preferably, the fatty acid salt (a), the alcohol or amine compound (b), and the artificial synthetic lipid or phospholipid (c) is used in a mole ratio of about 1:1:1. Usually, the tertiary amine (d) is contained at an amount of 0.01 to 1.0 mol, and more preferably 0.1 to 0.5 mol with respect to 1 mol fatty acid salt (a).

The above-described compounds (a) through (d) can be used alone or as a mixture of two or more, respectively.

As necessary, the bilayer membrane vesicle of the present invention may also include another compound capable of accumulating at an interface, or a compound that does not have the ability to accumulate at an interface but that can be included in a bilayer membrane. As will be described in detail later, examples include a fluorescent substance for observing membrane fusion.

The bilayer membrane vesicle of the present invention may be either a multilamellar vesicle (MLV: normally 0.2 to 5 μm in size) or a unilamellar vesicle (SUV: less than 100 nm; LUV and REV: 100 to 1000 nm; GUV: greater than 1000 nm). These can be produced by a general method employed by those skilled in the art. For example, an MLV can be produced as follows: each of compounds (a) through (d) is dissolved in an appropriate organic solvent (such as methanol or chloroform) and mixed in a container, and the organic solvents are evaporated. Next, the thin film formed on the inner wall is dried and then an appropriate aqueous solution (such as a phosphate buffer, a tris-hydrochloride buffer, or a carbonate buffer) was added thereto and the thin film was swelled by applying ultrasonic waves for about 30 seconds. The thin film was further stirred and shaken by a vortex mixer or the like to strip off the thin film, so that an MLV can be obtained as a suspension. For a SUV, by further applying strong ultrasonic waves at high output (for example, on ice for about 20 minutes) a SUV dispersion can be obtained (ultrasonic processing method). It is also possible to prepare a SUV, for example, by an ethanol injection method in which lipid dissolved in ethanol is injected using microsyringe into a buffer solution above its phase transition temperature, or by a French press method in which a MLV is placed into a French press and pressed. A LUV can be prepared by a method ordinarily used by those skilled in the art, such as the ether injection method, a surfactant method, a $Ca^{2+}$ fusion method, or a freeze-melt method. A REV is obtained by a reverse phase evaporation method. A GUV may be obtained, for example, by dialyzing an ethanol solution of a methyl glycoside and a lipid against a large amount of buffer solution.

The method of inducing a phase transition (for example, membrane fusion) of a bilayer membrane vesicle according to the present invention comprises:
  a step of preparing the bilayer membrane vesicle; and
  a step of adding a dehydrating condensing agent or a dehydrating condensing agent precursor to the bilayer membrane vesicle.

Examples of the dehydrating condensing agent used in the above method include water-soluble dehydrating condensing agents, dehydrating condensing agents capable of accumulating at an interface, and dehydrating condensing agent precursors thereof.

An example of a water-soluble dehydrating condensing agent is the quaternary ammonium salt represented by the following formula IV:

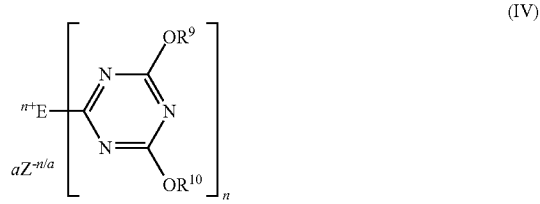

(IV)

wherein E is a monovalent or a divalent organic group having one or two tertiary amino groups; n is 1 when E has one tertiary amino group, and is 2 when E has two tertiary amino groups; $R^9$ and $R^{10}$ are each independently alkyl groups having 1 to 4 carbon atoms, or aryl groups having 6 to 8 carbon atoms; a is 1 or 2, and is 1 when n is 1; and $Z^{-(n/a)}$ is a counter anion having a valency of (n/a) (see WO 00/53544 and Kunishima et al., Tetrahedron, (2001) vol. 57, pp. 1551-1558). A specific example is 4-(4,6-dimethoxy-1,3,5-triazin-2-yl)-4-methylmorpholium chloride (DMT-MM).

An example of a dehydrating condensing agent capable of accumulating at an interface is a 1,3,5-triazin compound represented by the following formula V:

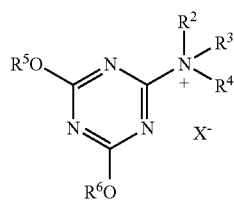

(V)

wherein $R^5$ and $R^6$ are each independently a methyl group, an ethyl group, a hydroxyalkyl group having 2 to 5 carbon atoms, $-(CH_2CH_2O)_mR^7$ (where m is an integer of 1 to 120, and $R^7$ is a hydrogen atom, a methyl group, an ethyl group, or a propyl group), $-(CH_2CH_2NR^8)_mH$ (where m is an integer of 1 to 120, and $R^8$ is an alkyl group having 2 to 5 carbon atoms, an N,N-dialkylaminoethyl group, or $-CH_2CH_2N^+(CH_3)_3$), $-CH_2CH_2SO_3^-$, $-CH_2CH_2N^+(CH_3)_3$, or an alkyl group having 6 to 20 carbon atoms, but both $R^5$ and $R^6$ are not an alkyl group having 6 to 20 carbon atoms at the same time; one or two of $R^2$, $R^3$, and $R^4$ is (are) a methyl group, and the remaining $R^2$, $R^3$, and $R^4$ is (are) each independently $-CH_2COO-C_nH_{2n+1}$, $-C_nH_{2n+1}$, or $-C_6H_4$-p-$C_nH_{2n+1}$, where n is an integer of 6 to 20 and $-C_nH_{2n+1}$ is linear; and $X^-$ is a halogen ion. The compound represented by the formula V is obtained by mixing, in an appropriate solvent, a cyanuric acid derivative represented by the following formula III:

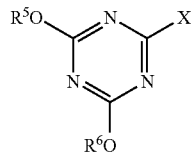

(III)

wherein $R^5$ and $R^6$ are each independently a methyl group, an ethyl group, a hydroxyalkyl group having 2 to 5 carbon atoms, $-(CH_2CH_2O)_mR^7$ (where m is an integer of 1 to 120, and $R^7$ is a hydrogen atom, a methyl group, an ethyl group, or a propyl group), $-(CH_2CH_2NR^8)_mH$ (where m is an integer of 1 to 120, and $R^8$ is an alkyl group having 2 to 5 carbon atoms, an N,N-dialkylaminoethyl group, or $-CH_2CH_2N^+(CH_3)_3$), $-CH_2CH_2SO_3^-$, $CH_2CH_2N^+(CH_3)_3$, or an alkyl group having 6 to 20 carbon atoms, but both $R^5$ and $R^6$ are not an alkyl group having 6 to 20 carbon atoms at the same time; and X is a halogen atom, and the tertiary amino represented by the following formula II:

(II)

wherein $R^2$, $R^3$, and $R^4$ are as defined above. In particular, it is preferable that the cyanuric acid derivative and the tertiary amine are mixed together at the same time where at least two compounds to be subject to dehydrating condensation are mixed.

Although it is possible to directly use the 1,3,5-triazin compound represented by the formula V as a dehydrating condensing agent, as described above, it is preferable that this compound is added at the same time where the vesicle is prepared, and thus control of fusion or phase transitions is difficult. Accordingly, it is preferable to add the cyanuric acid derivative (compound III), which is a dehydrating condensing agent precursor, to a vesicle that has been prepared so as to include the tertiary amine compound (d) as a component of the membrane in advance. In this case, by adding the cyanuric acid derivative (compound III) after the liposome has been prepared, the dehydrating condensing agent (compound V) can be produced within the system (liposome interface) to cause dehydrating condensation at the interface. Thus, this is more preferable for appropriately performing fusion or phase transition of interest.

In the formula III, when $R^5$ and $R^6$ each are a hydroxyalkyl group havinf 2 to 5 carbon atoms, the hydroxyalkyl group may be linear, branched, or cyclic, and there are no particular restrictions regarding the position and the number of hydroxyl groups. Preferably it is linear and has a terminal hydroxyl group. Examples of hydroxyalkyl groups having 2 to 5 carbon atoms include 2-hydroxyethyl, 3-hydroxypropyl, 4-hydroxylbutyl, and 5-hydroxypentyl.

In the formula III, when $R^5$ and $R^6$ are $-(CH_2CH_2O)_mR^7$, m is an integer of 1 to 120, and preferably an integer of 1 to 50. $R^7$ is a hydrogen atom, a methyl group, an ethyl group, or a propyl group. In this case, the average molecular weight of the $R^5$ and $R^6$ moieties is preferably from about 45 to about 5000 (which corresponds to m of 1 to 120), and more preferably from about 45 to about 2000 (which corresponds to m of 1 to 50).

In the formula III, when $R^5$ and $R^6$ are $-(CH_2CH_2NR^8)_mH$, m is an integer of 1 to 120, and preferably an integer of 1 to 50. $R^8$ is an ethyl group or an N,N-dialkylaminoethyl group in which the number of carbon atoms in the alkyl is from 2 to 5. In this case, the average molecular weight of the $R^5$ and $R^6$ moieties is preferably from about 45 to about 5000 (which corresponds to m of 1 to 120), and more preferably from about 45 to about 2000 (which corresponds to m of 1 to 50).

In the formula III, when $R^5$ and $R^6$ are alkyl groups having 6 to 20 carbon atoms, the alkyl group can be linear, branched, or cyclic. Preferably it is linear. Examples of the alkyl group having 6 to 20 carbon atoms of $R^5$ and $R^6$ include n-hexyl, n-pentyl, n-octyl, n-nonyl, n-decyl, n-dodecyl, and n-hexadecyl.

With regard to $R^5$ and $R^6$ of the formula III, in view of the fact that the cyanuric acid derivative can be easily retained at the water interface, it is preferable that the $R^5O-$ and the $R^6O$— moieties are hydrophilic. Although varying depending on the combination with the $R^2$, $R^3$, and $R^4$, it is preferable that at least one of $R^5$ and $R^6$ is a methyl group or an ethyl group, and more preferably both are methyl groups. It is not preferable that $R^5$ and $R^6$ are both alkyl groups having 6 to 20 carbon atoms at the same time, because the cyanuric acid derivative becomes strongly hydrophobic and makes accumulation at the water interface difficult.

Examples of the cyanuric acid derivative include 2-chloro-4,6-dimethoxy-1,3,5-triazin (CDMT).

As described above, to cause dehydrating condensation, it is particularly preferable to use the cyanuric acid derivative (compound III), which is a dehydrating condensing agent precursor, for a bilayer membrane vesicle containing the tertiary amine (d) as a component of the membrane of the vesicle, in view of the fact that it has a good property of accumulating at an interface of the bilayer membrane vesicle and that the dehydrating condensing agent can be produced at the interface.

In this step, the dehydrating condensing agent or the dehydrating condensing agent precursor is used in 1 to 100 equivalents, preferably 25 to 50 equivalents, with respect to the fatty acid salt (a) or the alcohol or amine compound (b). The temperature at which this step is performed can be suitably determined depending on the purpose, and usually the step is performed at room temperature. The time required for this step varies depending on various factors, such as the components of the membrane of the vesicle, the amount of the dehydrating condensing agent or the dehydrating condensing agent precursor, and the temperature at which the step is performed, and it can be adjusted in accordance with these factors.

When a cyanuric acid derivative is used in this step, as shown in the following scheme, first, by adding the cyanuric acid derivative of the formula III, a dehydrating condensing agent is formed along with the tertiary amine (d) that is present in the bilayer membrane vesicle. Then, the carboxylic acid (a) and the amine compound (dihydric alcohol) (b) in the membrane undergo dehydrating condensation to form a pseudo-ceramide. Thus, as described above, a change in the curvature of the vesicle, for example, occurs due to the increase in the critical load parameter of the membrane and the decrease in repulsion between membranes, and this causes a phase transition such as fusion of the membrane (see FIG. 1).

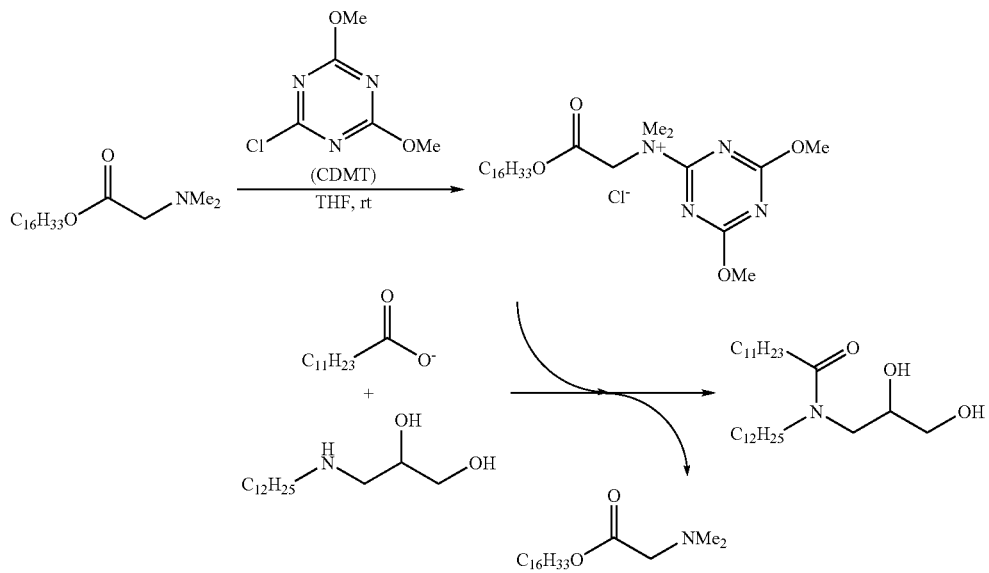

Figure 2:
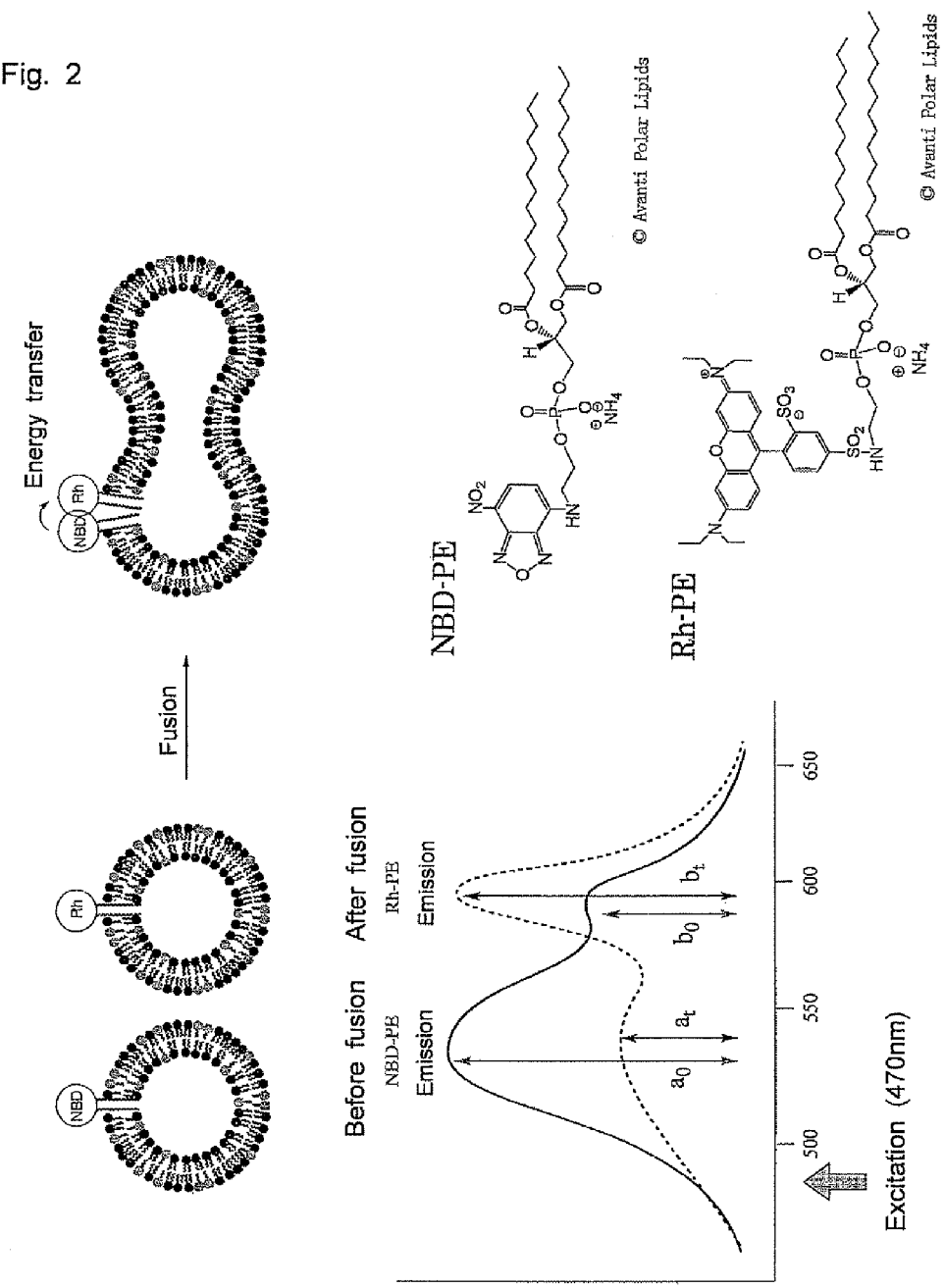
FIG. 2 is a fluorescence spectrum of the fluorescence energy transfer from NBD-PE to Rh-PE.

Examples of means for evaluating and observing a phase transition such as fusion of the membranes include observation by electron microscope, quantification of the produced pseudo-ceramide (for example, by mass spectrometry), and measurement of the change in fluorescence. In the case of measuring changes in fluorescence, a compound which causes a fluorescence energy transfer to another compound that present in the vicinity of the compound is introduced as a component of the bilayer membrane. Examples of such compounds include the combination of 1,2-dimyristyl-sn-glycero-3-phosphoethanolamine-N-(7-nitro-2-1,3-benzoxadiazol-4-yl) (NBD-PE) and 1,2-dimyristyl-sn-glycero-3-phosphoethanolamine-N-(lissamine rhodamine B sulfonyl) (Rh-PE). The former is the energy donor, and the latter is the energy acceptor. As shown in FIG. 2, a fluorescence energy transfer occurs when both NBD-PE and Rh-PE are present in the vicinity. As for evaluating changes in the fluorescence, it is possible to use the fluorescence change F that is obtained by:

$$\text{Fluorescence change } (F) = \frac{b_t/b_0}{a_t/a_0}$$

$a_0$=NBD-PE fluorescence intensity at start of the reaction
$a_t$=NBD-PE fluorescence intensity at given time
$b_0$=Rh-PE fluorescence intensity at start of the reaction
$b_t$=Rh-PE fluorescence intensity at given time For example, when NBD-PE and Rh-PE are included in separate vesicles, the F value increases by fusion of the vesicles. To the contrary, when a vesicle including both NBD-PE and Rh-PE fuses with a vesicle including neither, the distance between the NBD-PE and Rh-PE increases so that the F value decreases.

A phase transition, such as fusion of a membrane, according to the method of the present invention can occur not only between unstable bilayer membrane vesicles that include a fatty acid salt and an amine as membrane components and that can be activated by dehydrating condensation, such as those provided by the present invention, but also between such an unstable bilayer membrane vesicle and an inactive and stable bilayer membrane vesicle. The phase transition can be controlled through various factors, such as the ratio of the amount of the unstable bilayer membrane vesicles and the stable bilayer membrane vesicles, and the amount of the dehydrating condensing agent or the dehydrating condensing agent precursor.

Further, according to the method of the present invention, in a case where bilayer membrane vesicles have been induced to undergo their membrane fusion, membrane fusion can occurs without leaking of their contents.

Thus, according to the method of the present invention, it is possible to induce and control membrane fusion, for example, between a cell and a bilayer membrane vesicle that is provided by the present invention, so as to deliver the contents of the vesicle into the cell at appropriate timing.

EXAMPLES

Manufacturing Example 1

Synthesis of a Dihydric Alcohol

As shown in Scheme 1 below, a pseudo-sphingosine that is an amine having two hydroxyl groups as polar groups was synthesized by reacting a glycidol epoxide with a long-chain primary amine, which constitutes a liposome and is used as a substrate for dehydrating condensation within the liposome.

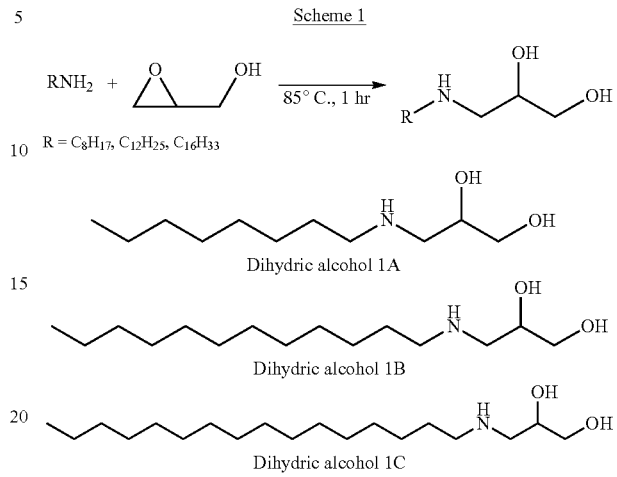

[1-1] Synthesis of 3-octylamino-1,2-propanediol (Dihydric Alcohol 1A)

n-Octylamine (3.0 g, 0.023 mol) was placed to a reaction vessel and heated to 85° C. Glycidol (1.56 g, 0.021 mol) was added thereto over 10 minutes under nitrogen gas stream and stirred for one hour, then the reaction mixture was dried in a vacuum. The resultant residue was subjected to column chromatography, developed with chloroform:methanol=1:1 (1% trimethylamine added), and then eluted and fractionated with methanol (1% trimethylamine added) to give dihydric alcohol 1A (1.03 g, yield 24%).

colorless crystal; melting point: 59.5 to 61.5° C. $^1$H NMR (CDCl$_3$) δ 0.87 (t, J=6.9 Hz, 3H), 1.21-1.35 (m, 10H), 1.42-1.51 (m, 2H), 2.54-2.73 (m, 3H), 2.79-2.85 (m, 1H), 3.58-3.65 (m, 1H), 3.70-3.77 (m, 2H); IR (KBr) 3320, 3271, 2919, 2853 cm$^{-1}$.

The solubility of the dihydric alcohol 1A against the buffer (5 mM NaH$_2$PO$_4$, 0.15 M NaCl, pH 7.5) used in the examples was about 10 mM.

[1-2] Synthesis of 3-dodecylamino-1,2-propanediol (Dihydric Alcohol 1B)

This compound was synthesized by the same method as employed to synthesize the dihydric alcohol 1A in [1-1] above (yield 33%).

colorless crystal; melting point: 78 to 79° C. $^1$H NMR (CDCl$_3$) δ 0.88 (t, J=6.9 Hz, 3H), 1.23-1.33 (m, 18H), 1.42-1.51 (m, 2H), 2.54-2.73 (m, 3H), 2.79-2.86 (m, 1H), 3.59-3.65 (m, 1H), 3.70-3.77 (m, 2H); IR (KBr) 3323, 3272, 2916, 2847 cm$^{-1}$; elemental analysis for C$_{15}$H$_{33}$NO$_2$: calculated: H, 12.82; C, 69.45. Found: H, 12.83; C, 69.42. ESI-MS m/z 260 [(M+1)$^+$, C$_{15}$H$_{33}$O$_2$N].

The solubility of the dihydric alcohol 1B against the buffer (5 mM NaH$_2$PO$_4$, 0.15 M NaCl, pH 7.5) used in the examples was about 0.2 mM.

[1-3] Synthesis of 3-hexadecylamino-1,2-propanediol (Dihydric Alcohol 1C)

This compound was synthesized by the same method as employed to synthesize the dihydric alcohol 1A [1-1] above (yield 34%).

colorless crystal; melting point: 86 to 89.5° C. $^1$H NMR (CDCl$_3$) δ 0.87 (t, J=6.9 Hz, 3H), 1.23-1.33 (m, 26H), 1.42-1.52 (m, 2H), 2.54-2.73 (m, 3H), 2.80-2.87 (m, 1H), 3.59-3.66 (m, 1H), 3.70-3.77 (m, 2H); IR (KBr) 3345, 3272, 2918, 2851 cm$^{-1}$; elemental analysis for C$_{19}$H$_{41}$NO$_2$: calculated: H, 13.10; C, 72.32. Found: H, 13.34; C, 72.30. ESI-MS m/z 316 [(M+1)$^+$, C$_{19}$H$_{41}$O$_2$N].

Manufacturing Example 2

Synthesis of Pseudo-ceramide

Because the product by the dehydrating condensation in the liposome is thought to be a pseudo-ceramide (Scheme 2), a pseudo-ceramide was synthesized according to the method of Kunishima et al. described above as a sample in order to confirm the findings.

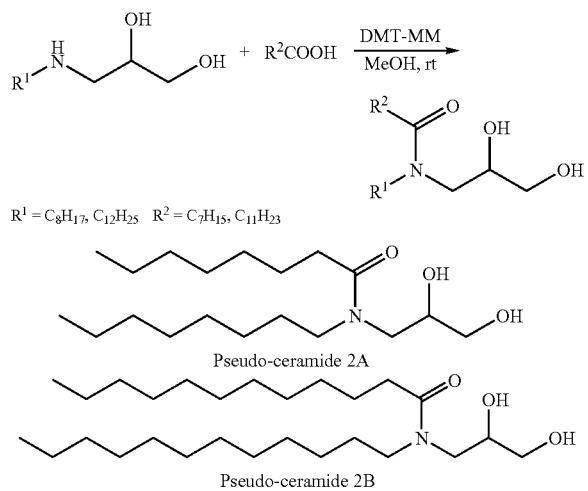

[2-1] Synthesis of 3-(N-lauroyldecylamino)-1,2-propanediol (Pseudo-ceramide 2B)

Sodium laurate (0.25 g, 1.13 mmol) was placed to a reaction vessel, and methanol (6 mL) was added thereto. The dihydric alcohol 1B that was obtained in [1-2] above (0.29 g, 1.13 mmol) was dissolved in methanol (4 mL) and added. DMT-MM (0.34 g, 1.24 mmol) was dissolved in methanol (2 mL) and added, and then this mixture was stirred at room temperature for five hours. The methanol was evaporated under reduced pressure with a pump, and then the residue was extracted using ethyl acetate and distilled water. The ethyl acetate layer was collected, washed twice with saturated sodium carbonate solution, once with distilled water, twice with 1 M HCl, once with distilled water, and then once with saturated saline, then dried over anhydrous magnesium sulfate, and the solvent was removed under reduced pressure. The resultant residue was subjected to column chromatography, developed with hexane:ethyl acetate=1:1 and then eluted and separated by hexane:ethyl acetate=4:6 to give pseudo-ceramide 2B (0.33 g, yield 65%).

colorless crystal; melting point: 35 to 36.5° C. $^1$H NMR (CDCl$_3$) δ 0.88 (t, J=6.9 Hz, 3H), 1.23-1.35 (m, 34H), 1.56-1.66 (m, 4H), 2.33 (t, J=7.6 Hz, 2H), 3.17-3.36 (m, 2H), 3.38-3.59 (m, 4H), 3.70-3.80 (1H); IR (KBr) 3354, 2919, 2851, 1613 cm$^{-1}$; elemental analysis for C$_{27}$H$_{55}$NO$_3$: calculated: H, 12.55; C, 73.41. Found: H, 12.71; C, 73.16. ESI-MS m/z 442 [(M+1)$^+$, C$_{27}$H$_{55}$O$_3$N].

[2-2] Synthesis of 3-(N-octanoyloctylamino)-1,2-propanediol (Pseudo-ceramide 2A)

This compound was synthesized by the same method as employed to synthesize the pseudo-ceramide 2B of [2-1] above (yield 52%).

colorless oil; $^1$H NMR (CDCl$_3$) δ 0.88 (t, J=7.0 Hz, 3H), 0.89 (t, J=6.9 Hz, 3H), 1.22-1.37 (m, 18H), 1.52-1.70 (m, 4H), 2.33 (t, J=7.6 Hz, 2H), 3.18-3.36 (m, 2H), 3.39-3.59 (m, 4H), 3.71-3.79 (m, 1H); IR (neat) 3378, 2926, 2855, 1620 cm$^{-1}$; elemental analysis for C$_{19}$H$_{39}$O$_3$N: calculated: H, 11.93; C, 69.25. Found: H, 12.14; C, 69.49. ESI-MS m/z 330 [(M+1)$^+$, C$_{19}$H$_{39}$O$_3$N].

Manufacturing Example 3

Synthesis of Tertiary Amine Capable of Accumulating at an Interface

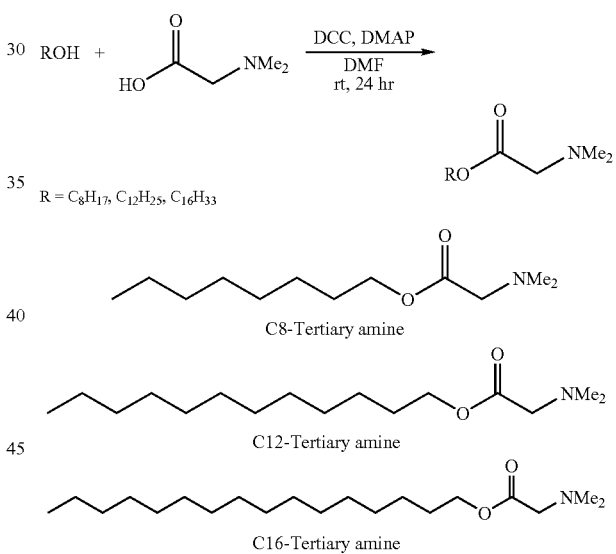

[3-1] Synthesis of N,N-dimethylamino-acetate-1-dodecyl Ester (C12-tertiary Amine)

First, 1-dodecyl alcohol (2.98 g, 0.016 mol), triethylamine (1.62 g, 0.016 mol) and 4-(N,N-dimethylamino)pyridine (DMAP; 0.195 g, 0.0016 mol) were added to a solution of N,N-dimethylglycine hydrochloride (2.23 g, 0.016 mol) in dry N,N-dimethylformamide (DMF; 100 mL) under nitrogen atmosphere, and cooled to 0° C. Then, dicyclohexylcarbodiimide (DCC; 3.63 g, 0.0176 mol) in dry DMF (60 ml) was added thereto at 0° C. The reaction mixture was returned to room temperature and stirred for about one day, then DMF was evaporated under reduced pressure with a pump. The residue was dissolved using ether and aqueous saturated sodium bicarbonate solution, and the ether layer was collected and washed once with water and once with saturated saline, after which it was dried over anhydrous magnesium sulfate, and then the solvent was removed under reduced pressure. The resultant residue was separated by column chromatography (hexane:ethyl acetate:triethylamine=50:50:1) to give N,N-dimethylamino-acetate-1-dodecyl ester (C12-tertiary amine) (yield 48%, 2.10 g).

colorless liquid. $^1$H NMR (CDCl$_3$) δ 0.88 (t, J=6.9 Hz, 3H), 1.23-1.31 (m, 18H), 1.59-1.68 (m, J=7.0 Hz, 2H), 2.35 (s, 6H), 3.15 (s, 2H), 4.12 (t, J=6.8 Hz, 2 h). ESI-MS m/z 272 [(M+1)$^+$, C$_{16}$H$_{33}$O$_2$N]. IR (KBr) 2923, 1749 cm$^{-1}$.

[3-2] Synthesis of
N,N-dimethylamino-acetate-1-octyl Ester
(C8-tertiary Amine)

The same procedure as in [3-1] above was performed except that 1-octyl alcohol was used instead of 1-dodecyl alcohol to give N,N-dimethylamino-acetate-1-octyl ester (C8-tertiary amine) at 59% yield.

colorless liquid. $^1$H NMR (CDCl$_3$) δ 0.88 (t, J=6.9 Hz, 3H), 1.24-1.33 (m, 10H), 1.57-1.66 (m, J=7.2 Hz, 2H), 2.35 (s, 6H), 3.16 (s, 2H), 4.12 (t, J=6.8 Hz, 2H). ESI-MS m/z 216 [(M+1)$^+$, C$_{12}$H$_{25}$O$_2$N]. IR (KBr) 2928, 1753 cm$^{-1}$.

[3-3] Synthesis of
N,N-dimethylamino-acetate-1-hexadeca ester
(C16-tertiary Amine)

The same procedure as in [3-1] above was performed except that cetyl alcohol was used instead of 1-dodecyl alcohol to give N,N-dimethylamino-acetate-1-hexadeca ester (C16-tertiary amine) at 44% yield.

colorless liquid. $^1$H NMR (CDCl$_3$) δ 0.87 (t, J=6.7 Hz, 3H), 1.23-1.30 (m, 26H), 1.59-1.68 (m, J=6.8 Hz, 2H), 2.35 (s, 6H), 3.16 (s, 2H), 4.12 (t, J=6.8 Hz, 2H). ESI-MS m/z 328 [(M+1)$^+$, C$_{20}$H$_{41}$O$_2$N]. IR (KBr) 2923, 1742 cm$^{-1}$.

Example 1

Preparation of Multilamellar Vesicle (MLV)
Including Tertiary Amine

MLV was prepared as follows, in accordance with a method set forth in the literature ("Kagaku to Seibutsu Jikken Line 27 Liposome no Chosei to Jikkenho", edited by Oku Naoto, Hirokawa Publishing, Chapter 5, p. 43).

Sodium laurate (45.0 mM in methanol, 8.7 μL), the dihydric alcohol 1B synthesized in [1-2] above (38.5 mM in chloroform, 10.1 μL), any one of the three tertiary amines synthesized in Manufacturing Example 3 (3.05 mM in chloroform, 25.6 μL), L-α-phosphatidylcholine (12.9 mM in chloroform, 28.5 μL), and the fluorescent agent NBD-PE (made by Avanti Polar Lipids) (1.23 mM in chloroform, 15.9 μL) were placed into a 20-mL eggplant-shaped flask. The solvent was evaporated under reduced pressure using a rotary evaporator, and then returned to atmospheric pressure with nitrogen gas, the thin film formed on the inner wall of the flask was further dried under reduced pressure at room temperature for 0.5 hours using a vacuum pump. The pressure in the flask was again restored to atmospheric pressure by nitrogen gas, 6 mL of phosphate buffer (5 mM NaH$_2$PO$_4$/Na$_2$HPO$_4$, 0.15 M NaCl, pH 7.5) was added thereto, and ultrasonic waves were applied for 30 seconds using a bath-type ultrasonic wave generation device, and then the flask was shaken (room temperature, 80% strength) for 20 minutes with a vortex mixer (AS ONE TUBE MIXER MODEL TMF was used) to strip off the thin film. The dispersion containing the thin film was transferred into a 10-mL sample vial followed by stirring with a vortex mixer (room temperature, 30% strength) for about half a day to give a NBD-PE-containing MLV dispersion that includes a tertiary amine.

A Rh-PE-containing MLV dispersion that includes a tertiary amine was obtained in the same manner as above, except that Rh-PE (made by Avanti Polar Lipids) (4.19 mM in chloroform, 4.7 μL) was used instead of NBD-PE as the fluorescent agent.

Example 2

Multilamellar Vesicle (MLV) Preparation-2

Various MLV dispersions that do not include a tertiary amine were obtained in the same manner as in Example 1, except that a tertiary amine was not placed into the 20-mL eggplant-shaped flask in the MLV preparation method of Example 1.

Example 3

Membrane Fusion Experiment Using Multilamellar
Vesicles (MLV)

First, 1 mL each of the MLV dispersions that contain a tertiary amine (C8 or C16) obtained in Example 1 were mixed at room temperature. A solution of 2-chloro-4,6-dimethoxy-1,3,5-triazin (CDMT) (150 mM or 300 mM) in methanol (21.7 μL) was added thereto, and allowed to stand at room temperature. Next, to the MLV dispersion obtained in Example 2, a solution of 4-(4,6-dimethoxy-1,3,5-triazin-2-yl)-4-methylmorpholium chloride (DMT-MM) (225 mM or 300 mM) in methanol (21.7 μL), which is a water-soluble dehydrating condensing agent, was added to prepare a mixture. As a control experiment, a mixture to which 21.7 μL of methanol was added instead of the CDMT solution was prepared.

The change in fluorescence over time of the prepared mixtures was measured with a fluorometer. The excitation wavelength was 470 nm. As mentioned above, the F value was used as the criterion for the change in fluorescence. When membrane fusion occurs, the F value increases (see FIG. 2). The results are shown in Table 1.

TABLE 1

| Condensing agent or precursor (equivalent)* | | Type of tertiary amine | Change in fluorescence (F value) | | | |
|---|---|---|---|---|---|---|
| CDMT | DMT-MM | in MLV | 2 hr | 5 hr | 12 hr | 36 hr |
| — | — | C16 | — | — | — | — |
| 25 | — | | 1.64 | 8.10 | — | — |
| 50 | — | | 4.41 | 10.4 | — | — |
| 50 | — | C8 | — | 2.22 | 5.40 | — |
| — | 38 | | — | — | — | 1.42 |
| — | 50 | | — | — | — | 1.64 |

*Amount with respect to sodium laurate

As shown in Table 1, it is found that in all cases where CDMT was used, the F value increases over time and membrane fusion occurs. On the other hand, with DMT-MM, membrane fusion occurred extremely slowly. When a condensing agent was not added, a change in fluorescence was not observed.

Example 4

Quantification of Pseudo-Ceramide 2B

In order to examine the relationship between the change in fluorescence and the reaction yield of the pseudo-ceramide in MLV fusion, the pseudo-ceramide produced in the MLV was quantified.

Figure 3:
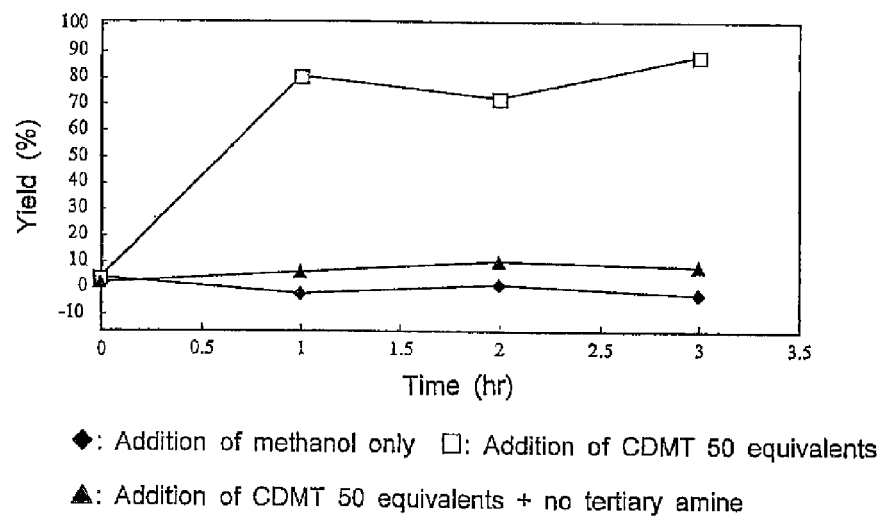
FIG. 3 is a graph showing the change over time in the yield of pseudo-ceramide produced in an MLV.

CDMT (150 mM or 300 mM in methanol, 21.7 µL) was added to 2 mL of a MLV dispersion containing a tertiary amine (C8 or C16) that was obtained in Example 1, and allowed to stand at room temperature. To the MLV dispersion that does not contain a tertiary amine that was obtained in Example 2, 21.7 µL of CDMT solution was added, and allowed to stand similarly. Another mixture was prepared by adding DMT-MM (300 mM in methanol, 21.7 µL) to the MLV dispersion that was obtained in Example 2. As a control experiment, 21.7 µL of methanol was added instead of the CDMT solution, and this was allowed to stand similarly. A portion of each MLV dispersion (500 µL) was taken at given times (2, 5, 12, and 36 hours), ammonium acetate (390 mM in distilled water, 8.3 µL) and N-methylmorpholine (NMM) (depending on the CDMT added, 0 µL, 3.6 µL, or 7.2 µL) were added thereto, followed by stirring for 10 minutes with a vortex mixer (room temperature, 30% strength). Then, 500 µL of ethyl acetate were added thereto, followed by stirring for 10 minutes with a vortex mixer (room temperature, 50% strength) to extract and perform to collect the organic layer. Then, 50 µL of the resultant organic layer, an internal standard (pseudo-ceramide 2A) solution (32.5 µM in ethyl acetate, 50 µL), 500 µL mixture of ammonium acetate aqueous solution (10 mM)/acetonitrile (1:10 (v/v)), and a sodium chloride aqueous solution (10 mM, 3.6 µL) were mixed, and quantified by ESI-MS measurement. For both the internal standard and the calibration substance, m/z 352 and 464, which were the sodium-added peaks (M+23), were used as a quantitative peak, respectively. The results are shown in FIG. 3 and Table 2.

TABLE 2

| Condensing agent or precursor (equivalent)* | | Type of tertiary amine in MLV | Yield of pseudo-ceramide (%) | | | |
|---|---|---|---|---|---|---|
| CDMT | DMT-MM | | 2 hr | 5 hr | 12 hr | 36 hr |
| 50 | — | C8 | — | 7 | 20 | — |
| 0 | — | C16 | 0 | 0 | — | — |
| 25 | — | | 42 | 92 | — | — |
| 50 | — | | 80 | 88 | — | — |
| 50 | — | | — | — | — | — |
| — | 50 | | — | — | — | 9 |

*Amount with respect to sodium laurate

When CDMT was added to the MLV dispersions that include a tertiary amine, a pseudo-ceramide was obtained at a yield according to the length of the lipid chain of the tertiary amine. When CDMT was not added, the production of a pseudo-ceramide was not observed. On the other hand, with DMT-MM, the pseudo-ceramide was produced extremely slowly. The results agreed with the results in Example 3 and thus a correlation between fusion and the amount of pseudo-ceramide produced was demonstrated. It should be noted that when CDMT was added to a MLV dispersion that does not contain a tertiary amine, the production of pseudo-ceramide was not observed.

Example 5

Change in Particle Size Accompanying MLV Fusion

A MLV dispersion was prepared according to the operation set forth in Example 1 using the compounds listed in Table 3 below.

TABLE 3

| | Concentration | Amount used |
|---|---|---|
| Sodium laurate | 45.0 mM (in methanol) | 21.7 µL |
| Dihydric alcohol 1B | 38.5 mM (in methanol) | 25.3 µL |
| C8-Tertiary amine | 4.64 mM (in methanol) | 42.0 µL |
| Nonreduced egg yolk lecithin | 12.9 mM (in methanol) | 75.6 µL | prepared by using 15 mL of phosphate buffer (5 mM NaH$_2$PO$_4$/0.15M NaCl, pH 8.5).

The MLV dispersion prepared was separated into 2 mL portions, and 50 equivalents (21.7 µL) CDMT (300 mM in methanol) was added thereto. For the control, 21.7 µL of methanol was added. Two samples were prepared and the particle size after 12 hours was measured by dynamic light scattering (DLS). The results are shown in Table 4.

TABLE 4

| Run | CDMT (equivalent) | Tertiary amine (equivalent) | Z average*[1] | |
|---|---|---|---|---|
| | | | 0 hr | 12 hr |
| 1 | 0 | 0.2 | 226.6 nm | 229.6 nm |
| 2 | 0 | 0.2 | 226.7 nm | 227.3 nm |
| 3 | 50 | 0.2 | 235.2 nm | 280.3 nm |
| 4 | 50 | 0.2 | 232.4 nm | 278.2 nm |

*[1]Z average = average diameter based on fluiddynamics

When CDMT was added, the particle size increased after 12 hours had elapsed, whereas when CDMT was not added, no change in the size was observed even after 12 hours. The fact indicates that membrane fusion is induced by the addition of CDMT.

Example 6

Preparation of Small Unilamellar Vesicle (SUV)

SUV were prepared as follows, in accordance with a method set forth in the literature ("Kagaku to Seibutsu Jikken Line 27 Liposome no Chosei to Jikkenho", edited by Oku Naoto, Hirokawa Publishing, Chapter 2, p. 27).

Sodium laurate (45.0 mM in methanol, 5.8 µL), the dihydric alcohol 1B (38.5 mM in chloroform, 6.8 µL), C16-tertiary amine (3.05 mM in chloroform, 17.0 µL), nonreduced egg yolk lecithin (13.0 mM in chloroform, 19.0 µL), and a fluorescent agent (for NBD-PE: 1.23 mM in chloroform, 10.6 µL; for Rh-PE: 4.19 mM in chloroform, 3.1 µL) were placed into a 20-mL eggplant-shaped flask, and the solvent was evaporated under reduced pressure using a rotary evaporator. The thin film formed on the inner wall of the flask was further dried under reduced pressure using a vacuum pump (room temperature, 0.5 hours). Then, 4 mL of phosphate buffer (5 mM NaH$_2$PO$_4$/Na$_2$HPO$_4$, 0.15 M NaCl, pH 8.5) was added thereto, and ultrasonic waves were applied for 30 seconds using a bath-type ultrasonic wave generation device. Next, the mixture was stirred and shaken for 10 minutes with a vortex mixer at 100% strength. Then, the mixture was transferred into a 20-mL test tube, and using a probe-type ultrasonic wave generation device (TOMY ULTRASONIC DISRUPTOR MODEL UR-200P), ultrasonic waves were applied (on ice) at 25 W for 20 minutes (one minute of application followed by 30 seconds rest, for a total application time of 20 minutes) to give a SUV dispersion.

Example 7

Membrane Fusion Experiment Using SUV

Figure 4:
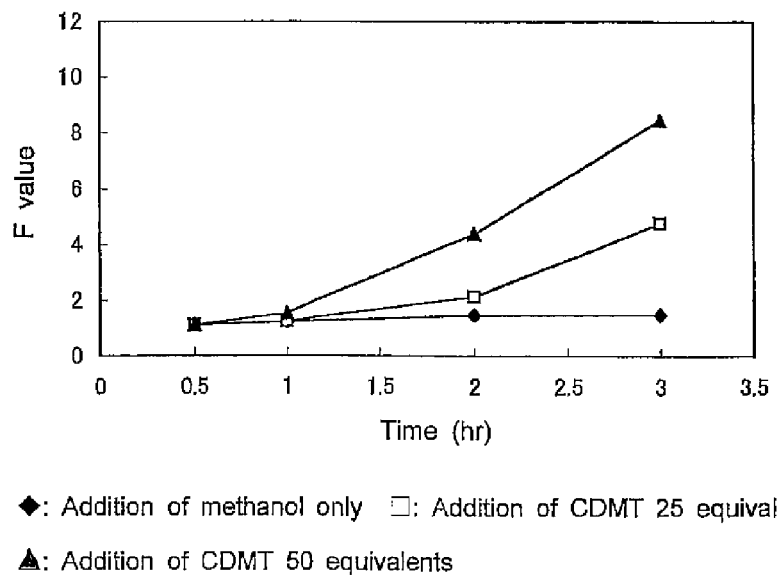
FIG. 4 is a graph showing the change in the F value over time due to SUV membrane fusion.

Using the SUV dispersion containing NBD-PE and Rh-PE obtained in Example 6, the change in fluorescence over time was measured in the same way as in the membrane fusion experiment with MLV of Example 3. The F value was calculated from the intensity of the fluorescence peaks to evaluate SUV fusion. The results are shown in FIG. 4. From the graph, it is suggested that membrane fusion occurred only when CDMT was added.

Example 8

Evaluation of SUV Membrane Fusion by a Fluorescence Dilution Method

An SUV dispersion with a fluorescent agent and an SUV dispersion without a fluorescent agent, of the compositions shown in Table 5 were prepared according to the SUV preparation method described in Example 6.

TABLE 5

| | SUV with fluorescent agent | | SUV without fluorescent agent | |
|---|---|---|---|---|
| | Concentration | Amount used | Concentration | Amount used |
| Sodium laurate | 45.0 mM (in methanol) | 5.8 μL | 45.0 mM (in methanol) | 7.2 μL |
| Dihydric alcohol 1B | 38.5 mM (in chloroform) | 6.8 μL | 38.5 mM (in chloroform) | 8.4 μL |
| C16-Tertiary amine | 3.05 mM (in chloroform) | 17.0 μL | 3.05 mM (in chloroform) | 21.3 μL |
| Nonreduced egg yolk lecithin | 13.0 mM (in chloroform) | 19.6 μL | 13.0 mM (in chloroform) | 25.0 μL |
| Fluorescent agent NBD-PE | 12.3 μM (in chloroform) | 351.1 μL | — | — |
| Rh-PE | 41.9 μM (in chloroform) | 21.0 μL | — | — |
| Phosphate buffer | * | 4 mL | * | 5 mL |

*: Phosphate buffer used was 5 mM NaH$_2$PO$_4$/0.15M NaCl, pH 8.5.

Figure 5:
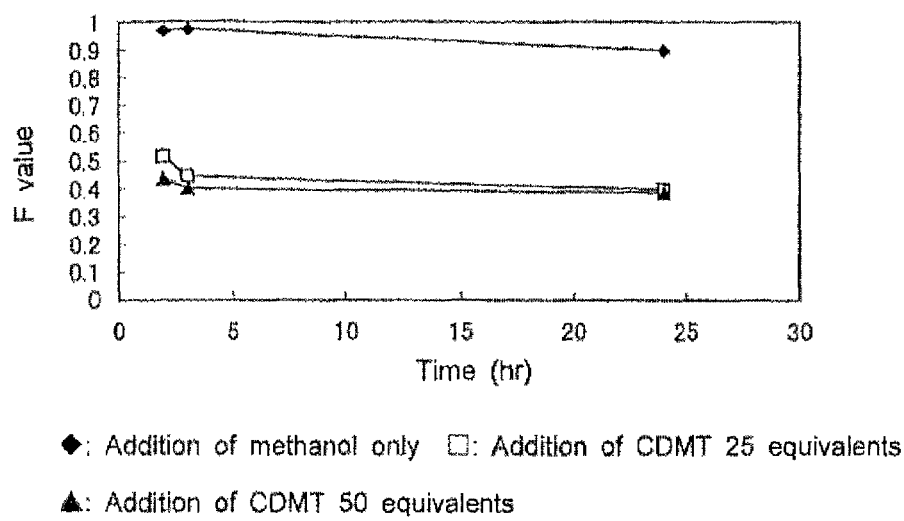
FIG. 5 is a graph showing the change in the F value over time due to SUV membrane fusion using the fluorescence dilution method.

First, 0.2 mL of the prepared SUV dispersion with a fluorescent agent and 1.8 mL of the SUV dispersion without a fluorescent agent were mixed at room temperature. Three samples were prepared for each SUV. To two of these samples 10.8 μL (25 equivalents) or 21.7 μL (50 equivalents) of CDMT (300 mM in methanol) was added respectively, and allowed to stand at room temperature. As a control experiment, 21.7 μL of methanol was added to the remaining sample, and also allowed to stand, and then the fluorescence was measured at a given time interval. The results are shown in FIG. 5.

Unlike the mixing method of Example 7, in the case of the fluorescence dilution method of Example 8, the F value becomes smaller as fusion proceeds. As shown in FIG. 5, a decrease in the fluorescence was found only when CDMT was added, and this strongly indicates that membrane fusion has been induced. It should be noted that in the graph of FIG. 5, it appears as if at initial state there is a difference between the control sample and the samples to which CDMT has been added. However, this indicates that a large change in fluorescence was observed two hours after CDMT addition, and thus there was no difference in the fluorescence before the start of the reaction.

Example 9

Change in Particle Size Accompanying SUV Fusion

The experiment was performed using two types of fatty acid salts, that is, sodium laurate and sodium oleate.
SUV dispersions with the compositions shown in Table 6 were prepared in accordance with the SUV preparation method described in Example 6.

TABLE 6

| | | SUV with sodium laurate | | SUV with sodium oleate | |
|---|---|---|---|---|---|
| | | Concentration | Amount used | Concentration | Amount used |
| Fatty acid | Sodium laurate | 22.5 mM (in methanol) | 20.2 μL | — | — |
| | Sodium oleate | — | — | 16.4 mM (in methanol) | 27.7 μL |
| Dihydric alcohol 1B | | 19.3 mM (in chloroform) | 23.5 μL | 19.3 mM (in chloroform) | 23.6 μL |
| C16-Tertiary amine | | 3.05 mM (in chloroform) | 29.8 μL | 3.05 mM (in chloroform) | 29.8 μL |

TABLE 6-continued

| | SUV with sodium laurate | | SUV with sodium oleate | |
|---|---|---|---|---|
| | Concentration | Amount used | Concentration | Amount used |
| Nonreduced egg yolk lecithin | 6.51 mM (in methanol) | 69.9 μL | 6.51 mM (in methanol) | 69.9 μL |
| Phosphate buffer | * | 7 mL | * | 7 mL |

* Phosphate buffer was prepared using 5 mM NaH$_2$PO$_4$/0.15M NaCl, pH 8.5.

The prepared SUV dispersions were filtered through a 0.45-μm pore size filter and each was divided into two 2 mL samples, one of which was supplied with 21.7 μL (50 equivalents) of CDMT (300 mM in methanol) and the other supplied with 21.7 μL of methanol as a control experiment, and allowed to stand at room temperature. The particle size after three hours was measured by DLS. The results are shown in Table 7.

TABLE 7

| Run | CDMT (equivalent) | Fatty acid | Z average*[1] 0 hr | 3 hr |
|---|---|---|---|---|
| 1 | 0 | Lauric acid | 91.3 nm | 91.6 nm |
| 2 | 50 | Lauric acid | 92.7 nm | 218.7 nm |
| 3 | 0 | Oleic acid | 65.6 nm | 66.3 nm |
| 4 | 50 | Oleic acid | 66.1 nm | 213.8 nm |

*[1]Z average = average diameter based on fluiddynamics

In both cases, the particle sizes were significantly increased at about 3 hours. The change in particle size indicates that about 10 to 20 of SUVs fused in the case of laurate, and about 30 to 40 of SUVs were fused in the case of oleate.

Example 10

Observation of SUV by Transmission Electron Microscope

A SUV dispersion of the composition shown in Table 8 was prepared in accordance with the SUV preparation method described in Example 6.

TABLE 8

|  | Concentration | Amount used |
|---|---|---|
| Sodium laurate | 22.5 mM (in methanol) | 288.9 μL |
| Dihydric alcohol 1B | 19.3 mM (in chloroform) | 336.8 μL |
| C16-Tertiary amine | 3.05 mM (in chloroform) | 426.2 μL |
| Nonreduced egg yolk lecithin | 6.51 mM (in methanol) | 998.5 μL | prepared in 5 mL of phosphate buffer (5 mM NaH$_2$PO$_4$/0.15M NaCl, pH 8.5).

Figure 6:
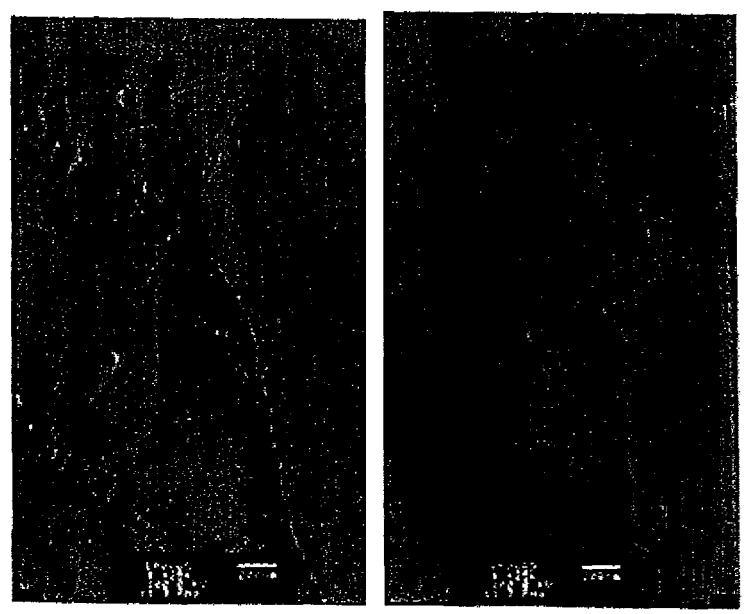
FIG. 6 is an electron micrograph of an SUV before CDMT addition.
Figure 7:
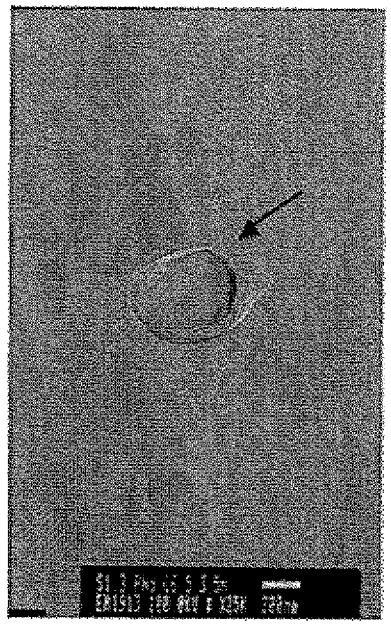
FIG. 7 is an electron micrograph of an SUV (GUV) after CDMT addition.
Figure 8:
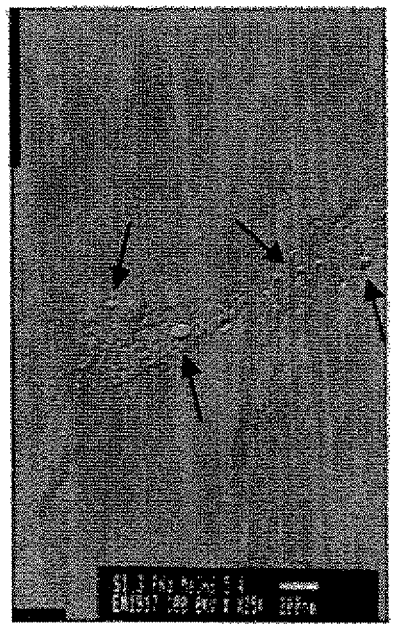
FIG. 8 is an electron micrograph of an SUV after the addition of methanol only.

To 200 μL of the prepared SUV dispersion, 4.3 μL of CDMT (300 mM in methanol) was added, and allowed to stand at room temperature. As a control experiment, 4.3 μL of methanol was added instead of CDMT, and allowed to stand at room temperature. Several drops of the SUV dispersion after standing were placed on a carrier, frozen with liquid nitrogen, and prepared specimens for electron microscopy (replicas) by a freeze fracturing method ordinarily performed by those skilled in the art (JEOL JFD-9010 was used). The specimens obtained were observed by TEM (JEOL JEM-1010) (acceleration voltage 100 kv). The electron micrographs are shown in FIGS. 6 to 8. The arrows in the micrographs indicate the SUV.

In cases where CDMT was added, the particle size was several 10 to about 100 nm prior to CMDT addition (FIG. 6), after CDMT addition it had significantly increased to greater than 1 μm, and the number of particles was noticeably decreased (FIG. 7). This is likely because several thousand SUVs in proximity one another fused together to form great GUVs. On the other hand, when only methanol was added, little change was observed in the particle size or distribution, even after more than one day (FIG. 8).

Example 11

Fusion Experiment Between Active SUV and Inactive SUV

An SUV dispersion with a fluorescent agent and an SUV dispersion without a fluorescent agent, of the compositions shown in Table 9 were prepared according to the SUV preparation method described in Example 6, for both a normal SUV (hereinafter, referred to as inactive SUV) and an SUV that include a fatty acid salt and an amine as components of the membrane and that also can be activated by dehydrating condensation (hereinafter, referred to as active SUV).

TABLE 9

|  |  | Active SUV with fluorecent agent | Active SUV without fluorecent agent | Inactive SUV with fluorecent agent | Inactive SUV without fluorecent agent |
|---|---|---|---|---|---|
| Sodium laurate |  | 13 nmol | 117 nmol | — | — |
| Dihydric alcohol 1B |  | 13 nmol | 117 nmol | — | — |
| C16-Tertiary amine |  | 2.6 nmol | 23.4 nmol | — | — |
| Nonreduced egg yolk lecithin |  | 13 nmol | 117 nmol | 28.6 nmol | 257.4 nmol |
| Fluorescent agent | NBD-PE | 0.39 nmol | — | 0.39 nmol | — |
|  | Rh-PE | 0.13 nmol | — | 0.13 nmol | — |
| Phosphate buffer* |  | 0.2 mL | 0.8 mL | 0.2 mL | 0.8 mL |

*Phosphate buffer used was 5 mM NaH$_2$PO$_4$/0.15M NaCl, pH 8.5.

In accordance with the fluorescence dilution method described in Example 8, 0.2 mL of the prepared SUV dispersion with a fluorescent agent and 1.8 mL of the SUV dispersion without a fluorescent agent were mixed at room temperature. Here, there were four combinations of SUVs, these being a combination of the active SUV with a fluorescent agent and the active SUV without a fluorescent agent (run 1), a combination of the inactive SUV with a fluorescent agent and the active SUV without a fluorescent agent (run 2), a combination of the active SUV with a fluorescent agent and the inactive SUV without a fluorescent agent (run 3), and a combination of the inactive SUV with a fluorescent agent and the inactive SUV without a fluorescent agent. Then, 15.2 μL (4.55 μmol: 35 equivalents of the total fatty acid salt of run 1) of CDMT (300 mM in methanol) was added thereto, allowed to stand at room temperature, and the change in the F values over time was measured with a fluorometer. The results are shown in FIG. 9.

Figure 9:
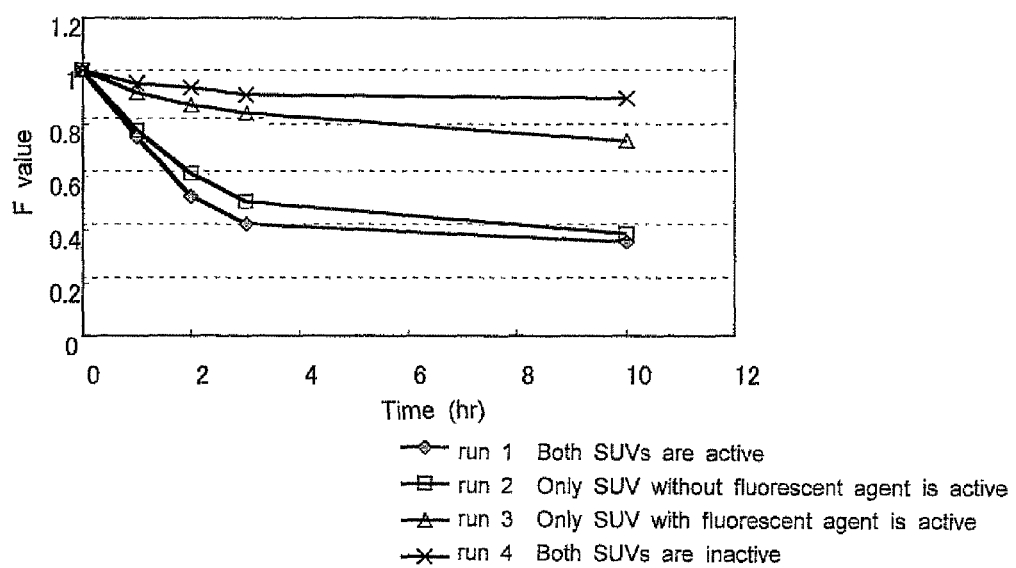
FIG. 9 is a graph showing the results of four combinations of SUVs and the change in the F values over time as measured with a fluorometer.

As shown in FIG. 9, the F value significantly changes even if one of the SUVs is an inactive SUV (runs 2 and 3). Since a fusion between identical SUVs theoretically should not result in a change in fluorescence, the decrease in the F value indicates that fusion between an active SUV and an inactive SUV was caused. The reason why the amount of change in the F value is smaller when there is less active SUV (run 3) is conceivably because the instability of the SUV is eliminated by a single fusion, and further fusion does not proceed, and thus the fluorescent agent was not sufficiently diluted. On the other hand, when 90% of the SUVs have been active (run 2), it is likely that fusion occurs in multiple stages and thereby the fluorescent agent is sufficiently diluted, and thus a large change in the F value appears.

Example 12

Examination of Leaking of Aqueous Phase within SUV Accompanying Fusion

To employ membrane fusion for the purpose of DDS or gene transfer, for instance, the liposome contents must be properly introduced into a target cell. In cases where fusion is accompanied by partial destruction of the membrane, many of the content leaks out and can no longer carry out its purpose, so that its applicability is limited. Accordingly, a test was performed to evaluate leaking of content at the time of fusion.

The fluorochrome calcein shown below is self-quenching and does not fluoresce at high concentrations, whereas it fluoresces at low concentrations.

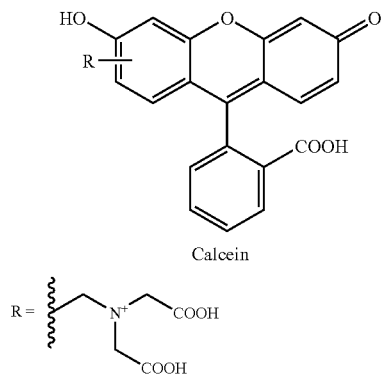

Calcein

Accordingly, in this example, by utilizing the property of the compound, a fusion test was performed for liposomes in which (in the inner aqueous phase) calcein has been contained at a high concentration in advance. If the contents leak out in conjunction with fusion, then the fluorescence by calcein is diluted in the outside aqueous phase is observed, whereas if leaking does not occur, no change in the fluorescence occurs.

The SUV was prepared according to the method described in Example 6. However, the calcein (75 mM) was added to a phosphate buffer (5 mM NaH$_2$PO$_4$/Na$_2$HPO$_4$, 0.15 M NaCl, pH 8), and ultrasonic wave treatment was performed to produce SUVs. The SUVs were separated by gel filter (Sephadex G-50, using the same phosphate buffer solution in the mobile phase) to remove the calcein present in the outside aqueous phase, giving a SUV dispersion.

CDMT (50 equivalents) was added to the obtained SUV dispersion, and allowed to stand at room temperature and the fluorescence (520 nm) was measured (Fs) after a given time, and immediately after Triton X-100 (10%, 200 μL) was added to destroy the SUV, and then the fluorescence was measured again ($F_T$). As a control experiment that does not accompany membrane fusion, the same SUV was used and the fluorescence was measured at a given interval without adding CDMT, and then lastly, Triton X-100 was added to destroy the liposome, and the fluorescence was measured. The rate of leakage was calculated by the following equation.

$$\text{Leakage of calcein (\%)} = \frac{F_S \times 1.01 - F_0}{F_T \times 1.11 - F_0} \times 100$$

$F_0$: Fluorescence intensity at 0 hours
$F_S$: Fluorescence intensity at each hour
$F_T$: Fluorescence intensity after adding Triton X-100

The results obtained are shown in Table 10 below.

TABLE 10

| | Rate of leakage (%) | |
| --- | --- | --- |
| Time | With fusion | Without fusion (control) |
| 1 hr | 6.5 | 1.3 |
| 2 hr | 7.1 | 2.0 |
| 3 hr | 8.3 | 2.2 |

As shown in Table 10, when CDMT has been added to undergo membrane fusion, although a slight increase in the rate of leakage is observed up to three hours later when fusion is substantially complete (2% in the case of the control experiment, 8% when fusion occurred), the fluorescence intensity ($F_S$) is significantly smaller than the fluorescence intensity ($F_T$) when TritonX-100 had been added immediately after measurement, and therefore it is found that there was substantially no leakage of the contents.

INDUSTRIAL APPLICABILITY

According to the method of the present invention, the dehydrating condensation reaction is utilized to chemically change the lipids forming a molecular aggregate so as to change the physical characteristics and morphology of the molecular aggregate, and thereby it is possible to control the timing of phase transitions such as membrane fusion, for example. In other words, in a bilayer membrane vesicle it is possible to induce a phase transition in a molecular aggregate, and thus it is possible to induce fusion or fission of the molecular aggregate at the water interface of a liposome, for instance. Furthermore, the bilayer membrane vesicles of the present invention can provide a vesicle in an activated or a semi-stable state. Further, at the time of membrane fusion of the liposome, for example, the contents of the liposome can be fused as well. Therefore, the method and the bilayer membrane vesicle of the present invention are useful for research in the field of organic synthesis chemistry and interface chemistry, which utilize dehydrating condensation, and the field of employing vesicles such as liposomes, for instance. It is useful as a model system for research regarding biological morphological changes, such as the formation, degradation, fission, and fusion of cells and cellular organelles, useful for elucidating biological mechanisms accompanying endocytosis and exocytosis, as well as useful in the development of medical treatments, such as gene therapy and drug delivery systems.

The invention claimed is:

1. A bilayer membrane vesicle, comprising molecular aggregates containing:
   (a) a fatty acid salt having 6 to 20 carbon atoms;
   (b) an alcohol or an amine compound having an aliphatic chain of 6 to 20 carbon atoms;
   (c) an artificial synthetic lipid or a phospholipid capable of forming a bilayer membrane; and (d) a tertiary amine compound represented by the following formula II:

(II)

wherein one or two of $R^2$, $R^3$, and $R^4$ is a methyl group, and the remaining $R^2 R^3$ and $R^4$ is each independently —$CH_2COOC_nH_{2n+1}$ or —$C_nH_{2n+1}$, or —$C_6H_4$-p-$C_nH_{2n+1}$, where n is an integer of 6 to 20, and —$C_nH_{2n+1}$ is linear.

2. The bilayer membrane vesicle of claim 1, wherein the (b) alcohol or amine compound is a dihydric alcohol represented by the following formula I:

$$R^1—NH—CH_2—CH(OH)—CH_2OH \quad (I)$$

wherein $R^1$ is an alkyl group having 6 to 20 carbon atoms, an alkenyl group having 6 to 20 carbon atoms, or an alkynyl group having 6 to 20 carbon atoms.

3. The bilayer membrane vesicle of claim 1, wherein the mole ratio of the (a) fatty acid salt and the (b) alcohol or amine compound is 1:1.

4. The bilayer membrane vesicle of claim 1, wherein the mole ratio of the (a) fatty acid salt, the (b) alcohol or amine compound, and the (c) artificial synthetic lipid or phospholipid capable of forming a bilayer membrane is 1:1:1.

5. The bilayer membrane vesicle of claim 1, wherein the (c) artificial synthetic lipid or phospholipid capable of forming a bilayer membrane is a phospholipid.

6. The bilayer membrane vesicle of claim 2, wherein the mole ratio of the (a) fatty acid salt and the (b) alcohol or amine compound is 1:1.

7. The bilayer membrane vesicle of claim 2, wherein the mole ratio of the (a) fatty acid salt, the (b) alcohol or amine compound, and the (c) artificial synthetic lipid or phospholipid capable of forming a bilayer membrane is 1:1:1.

8. The bilayer membrane vesicle of claim 3, wherein the mole ratio of the (a) fatty acid salt, the (b) alcohol or amine compound, and the (c) artificial synthetic lipid or phospholipid capable of forming a bilayer membrane is 1:1:1.

9. The bilayer membrane vesicle of claim 2, wherein the (c) artificial synthetic lipid or phospholipid capable of forming a bilayer membrane is a phospholipid.

\* \* \* \* \*

UNITED STATES PATENT AND TRADEMARK OFFICE
CERTIFICATE OF CORRECTION

PATENT NO.         : 8,449,979 B2  Page 1 of 1
APPLICATION NO.    : 11/814901
DATED              : May 28, 2013
INVENTOR(S)        : Munetaka Kunishima It is certified that error appears in the above-identified patent and that said Letters Patent is hereby corrected as shown below:

Title Page, Column 2, Foreign Patent Documents, item (56), Line 2, below "EP 1138310 A1 3/2000" delete "EP 1085000 A1 3/2001"

Title Page 2, Column 1, Foreign Patent Documents, item (56), Line 2, above "FR 2803202 A1 7/2001" delete "FR 2803202 A1 1/2000"

Title Page 2, Column 1, Foreign Patent Documents, item (56), Line 4, above "FR 2842734 A1 1/2004" delete "FR 2842734 A1 7/2002"

Title Page 2, Column 1, Foreign Patent Documents, item (56), Line 9, above "JP 2001089360 A1 4/2001" delete "JP 2001089360 A1 3/2001"

In the Claims:

Column 27, Line 11, Claim 1, delete "$R^2\ R^3$" and insert -- $R^2, R^3$ --

Signed and Sealed this
Twelfth Day of November, 2013

Teresa Stanek Rea
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,449,979 B2 | Page 1 of 1 |
| APPLICATION NO. | : 11/814901 | |
| DATED | : May 28, 2013 | |
| INVENTOR(S) | : Munetaka Kunishima | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,263 days.

Signed and Sealed this
Twenty-eighth Day of July, 2015

Michelle K. Lee
*Director of the United States Patent and Trademark Office*